United States Patent
Altschuler et al.

(10) Patent No.: US 8,808,725 B2
(45) Date of Patent: Aug. 19, 2014

(54) SOLID FORMS FOR TISSUE REPAIR

(75) Inventors: Nir Altschuler, Hod Hasharon (IL); Razi Vago, Lehavim (IL)

(73) Assignee: Cartiheal (2009) Ltd., Ariel (IL)

( * ) Notice: Subject to any disclaimer, the term of this patent is extended or adjusted under 35 U.S.C. 154(b) by 330 days.

(21) Appl. No.: 13/130,272

(22) PCT Filed: Nov. 19, 2009

(86) PCT No.: PCT/IL2009/001092
§ 371 (c)(1),
(2), (4) Date: Jul. 8, 2011

(87) PCT Pub. No.: WO2010/058400
PCT Pub. Date: May 27, 2010

(65) Prior Publication Data
US 2011/0256228 A1     Oct. 20, 2011

Related U.S. Application Data

(60) Provisional application No. 61/116,503, filed on Nov. 20, 2008.

(51) Int. Cl.
| | | |
|---|---|---|
| A61K 33/00 | (2006.01) | |
| A61P 19/02 | (2006.01) | |
| A61P 19/00 | (2006.01) | |
| A61P 19/08 | (2006.01) | |
| A61K 9/00 | (2006.01) | |

(52) U.S. Cl.
USPC ............................ 424/423; 424/400; 424/93.7

(58) Field of Classification Search
CPC ... A61K 35/12; A61K 38/1875; A61K 35/32; A61K 38/17
USPC ......................................... 424/423, 400, 93.7
See application file for complete search history.

(56) References Cited

U.S. PATENT DOCUMENTS

| | | | |
|---|---|---|---|
| 6,995,013 | B2 | 2/2006 | Connelly et al. |
| 2002/0183858 | A1* | 12/2002 | Contiliano et al. ........ 623/23.76 |
| 2003/0236573 | A1 | 12/2003 | Evans et al. |
| 2007/0190099 | A1* | 8/2007 | DiBenedetto et al. ........ 424/422 |
| 2008/0065210 | A1 | 3/2008 | McKay |
| 2008/0249632 | A1 | 10/2008 | Stone et al. |
| 2008/0281431 | A1 | 11/2008 | Missos |

FOREIGN PATENT DOCUMENTS

WO     99/02200 A2     1/1999

OTHER PUBLICATIONS

Abramovitch-Gottlib, L., et al., "Biofabricated marine hydrozoan: a bioactive crystallinie material promoting ossification of mesenchymal stem cells," *Tissue Engineering* (2006) 12(4):729-739.
Guillemin, G., et al., "Comparison of coral resorption and bone apposition with two natural corals of different porosities," *J. Biomed. Mater. Res.* (1989) 23(7):765-779.
Peretz, H., et al., "Superior survival and durability of neurons and astrocytes on 3-dimensional aragonite biomatrices," *Tissue Engineering* (2007) 13(3):461-472.
Petite, H., et al., "Tissue-engineered bone regeneration," *Nature Biotechnology* (2000) 18(9):959-963.
Tang, Y., et al., "A study on repairing mandibular defect by means of tissue-engineering and human bone morphogenetic protein-2 gene transfection in osteoporotic rats," *Zhonghua Kou Qiang Yi Xue Za Zhi* (2006) 41(7):430-431. (English abstract in document).
Vago, Razi, "Beyond the skeleton: Cnidarian biomaterials as bioactive extracellular microenvironments for tissue engineering," *Organogenesis* (2008) 4(1):18-22.
U.S. Appl. No. 13/378,474, 371(c), filed Mar. 5, 2012.
U.S. Appl. No. 13/378,458, 371(c), filed Mar. 13, 2012.

* cited by examiner

*Primary Examiner* — Frederick Krass
*Assistant Examiner* — Tracy Lu
(74) *Attorney, Agent, or Firm* — Alston & Bird LLP

(57) ABSTRACT

This invention provides coral-based scaffolds for cartilage repair, and instruments for insertion and utilization of same within a site of cartilage repair.

26 Claims, 12 Drawing Sheets

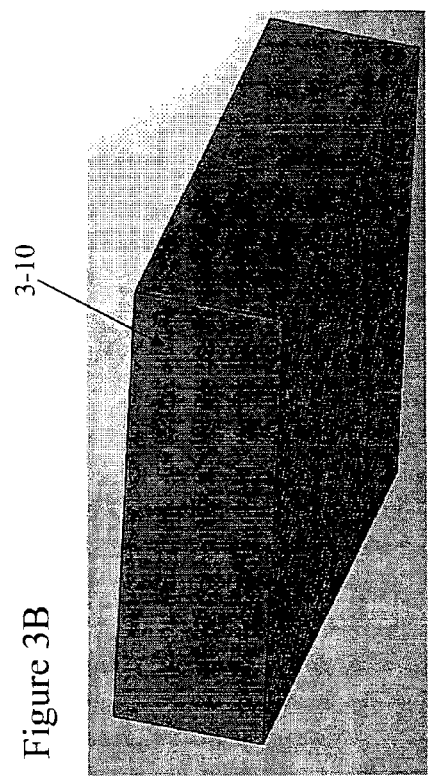
Figure 3B
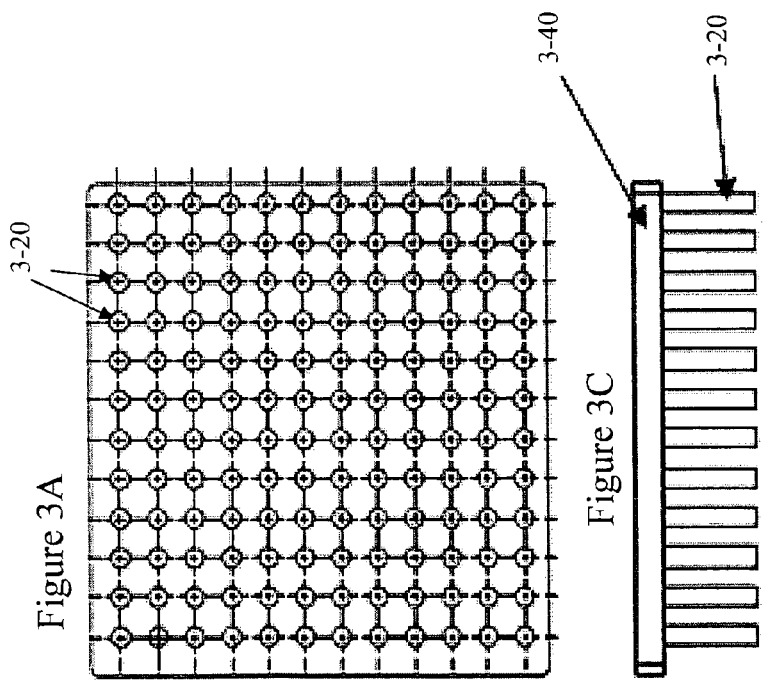
Figure 3A
Figure 3C

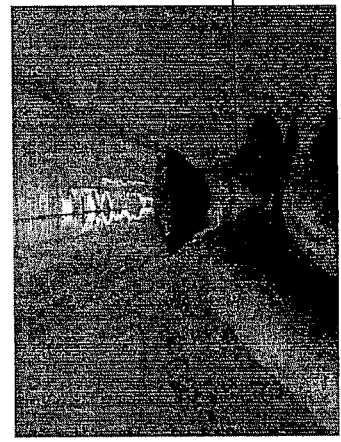
Figure 5B
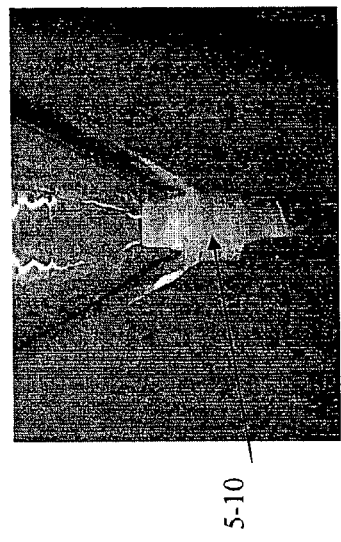
Figure 5A
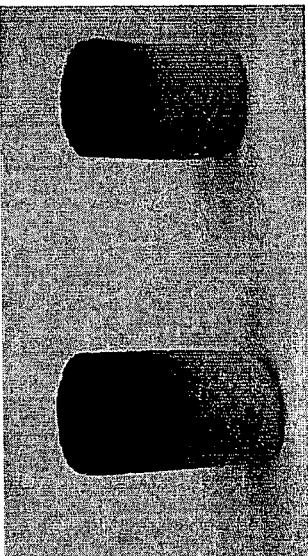
Figure5E
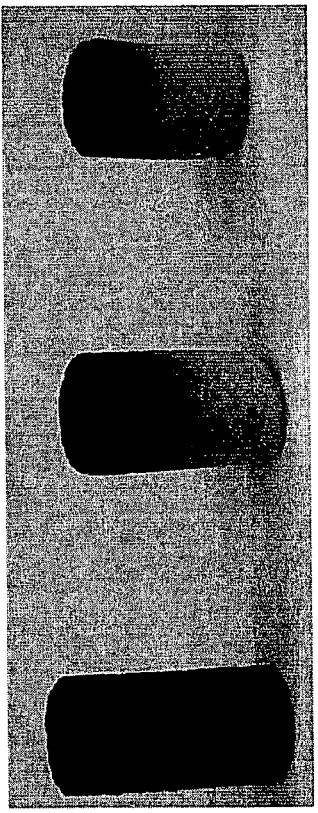
Figure5D
Figure5C 1% gel 8-10

3% gel

Figure 11A
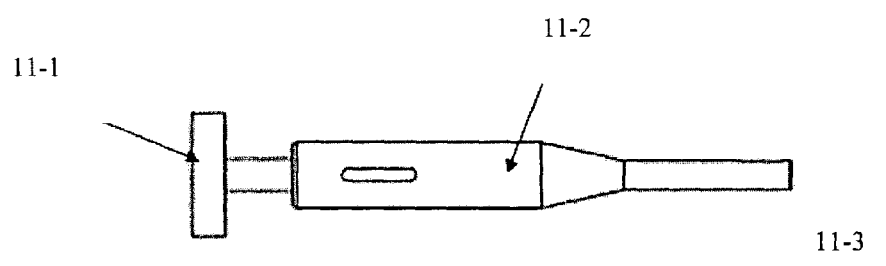
Figure 11B
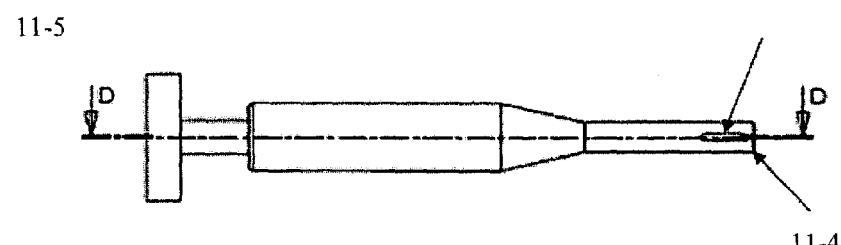
SECTION D-D
Figure 11C

SECTION D-D

SOLID FORMS FOR TISSUE REPAIR

BACKGROUND OF THE INVENTION

Defects and degeneration of the articular cartilage surfaces of joints causes pain and stiffness. Damage to cartilage which protects joints can result from either physical injury as a result of trauma, sports or repetitive stresses (e.g., osteochondral fracture, secondary damage due to cruciate ligament injury) or from disease (e.g. osteoarthritis, rheumatoid arthritis, aseptic necrosis, osteochondritis dissecans, avascular necrosis).

Osteoarthritis (OA) results from general wear and tear of joints, most notably hip and knee joints. Osteoarthritis is common in the elderly but, in fact, by age 40 most individuals have some osteoarthritic changes in their weight bearing joints. Another emerging trend increasing the prevalence of osteoarthritis is the rise in obesity. The CDC estimates that 30% of American adults (or 60 million people) are obese. Obese adults are 4 times more likely to develop knee OA than normal weight adults. Rheumatoid arthritis is an inflammatory condition which results in the destruction of cartilage. It is thought to be, at least in part, an autoimmune disease with sufferers having a genetic predisposition to the disease.

Orthopedic prevention and repair of damaged joints is a significant burden on the medical profession both in terms of expense and time spent treating patients. In part, this is because cartilage does not posses the capacity for self-repair. Attempts to re-grow hyaline cartilage for repair of cartilage defects remain unsuccessful.

Orthopedic surgery is available in order to repair defects and prevent articular damage in an effort to forestall serious degenerative changes in a joint. The use of surgical techniques often requires the removal and donation of healthy tissue to replace the damaged or diseased tissue. Techniques utilizing donated tissue from autografts, allografts, or xenografts are wholly unsatisfactory as autografts add additional trauma to a subject and allografts and xenografts are limited by immunological reactivity to the host subject and possible transfer of infective agents. Surgical attempts to utilize materials other than human or animal tissue for cartilage regeneration have been unsuccessful.

SUMMARY OF THE INVENTION

In one embodiment, the present invention provides a scaffold for repair of cartilage comprising coral having at least a first portion of an exposed surface raised with respect to at least a second portion of the exposed surface in the coral, wherein the first portion comprises at least a region, which specifically positions and confines the coral at an optimal depth and angle within a site of cartilage repair.

In one embodiment, the present invention provides a method of inducing or enhancing cartilage repair, the method comprising implanting in a subject, a scaffold of this invention within a site of cartilage repair, wherein a region of the scaffold penetrates through a bone, resulting in this region inserting within a bone marrow, proximal to the site of cartilage repair.

In one embodiment, the present invention provides an instrument to aid in cartilage repair comprising at least one tool to guide a scaffold of this invention to an optimal depth at a site of cartilage repair, guide a scaffold of this invention to an optimal angle at a site of cartilage repair, or a combination thereof, optionally at least one tool to process a scaffold of this invention following implantation within a site of cartilage repair, optionally at least one tool to effect penetration of a scaffold of this invention through a bone, and insertion within a bone marrow, proximal to a site of cartilage repair and optionally at least one tool to release a scaffold of this invention at a site of cartilage repair, whereby said tool may be separated from said scaffold following placement of said scaffold within a site of cartilage repair.

In one embodiment, this invention provides a kit for repair of cartilage comprising a scaffold of this invention, a tool of this invention, and directions for utilizing the scaffold and the tool in tissue repair.

In one embodiment, this invention provides a scaffold for tissue repair, wherein the scaffold comprises a polymer form enveloping coral particles.

BRIEF DESCRIPTION OF THE DRAWINGS

FIG. 3A shows an embodiment of a scaffold of this invention in cross-sectional view. FIG. 3B shows an angled longitudinal filled in view of an embodiment of a scaffold of this invention and FIG. 3C shows a cross section along the Z axis of the scaffold. The scaffold comprises first regions 3-20 which are raised with respect to second regions 3-40.

FIGS. 5A-5B are photographs depicting the preparation of embodied scaffolds incorporating a polymer therewithin. FIG. 5A depicts fitting of the scaffold within a device used to prepare the polymer/coral scaffold, in this embodiment, a funnel and FIG. 5B depicts the effective selective incorporation within only a desired region of the scaffold. FIGS. 5C-5E depict various scaffold forms incorporating different amounts of the polymer as a consequence of the timing of application, as further described hereinunder.

FIG. 10 depicts an embodiment of a tool of this invention.

FIG. 11 schematically depicts another embodiment of a tool of this invention, where the figure depicts, for example, a tool insert, which may be inserted in the Harvester shown in FIG. 10A. The insertion body 11-2 depicted in FIG. 11A will further comprise a grooved hollow 11-3, which accommodates insertion of a scaffold as herein described within the hollow. The insertion body edge 11-4 is smooth. When the implant is loaded within the insert, the plunger or piston 11-1 pushes the implant out of the tool insert and into the site of repair, in for example, a hole made by the harvester of FIG. 10. FIG. 11C shows a cross section taken as indicated in FIG. 11B, showing positioning of the scaffold within the tool insert.

DETAILED DESCRIPTION OF THE PRESENT INVENTION

Figure 1A:
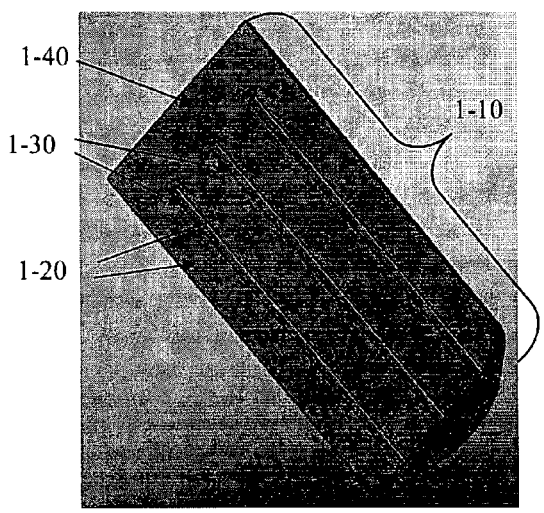
FIG. 1A shows a longitudinal filled in view of an embodiment of a scaffold of this invention. The scaffold comprises first regions 1-20 which are raised with respect to second regions 1-40, which first region in some embodiments is proximal to a void 1-30, which abuts the second region.
Figure 1B:
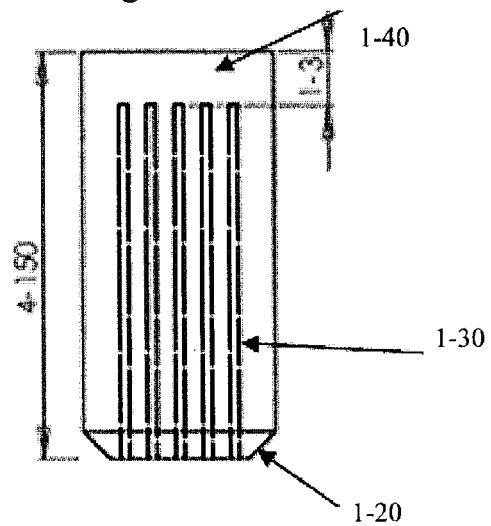
FIG. 1B shows a similar longitudinal view.
Figure 1C:
FIG. 1C shows a bottom angled view of the scaffold in FIG. 1A, where the hollows 1-20 are evident.
Figure 1D:
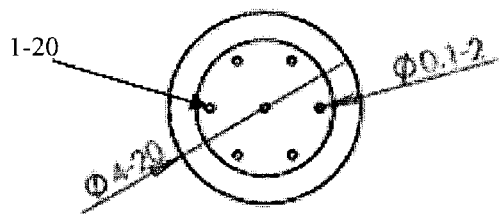
FIG. 1D shows a cross section of an edge of the scaffold in FIG. 1C.
Figure 1E:
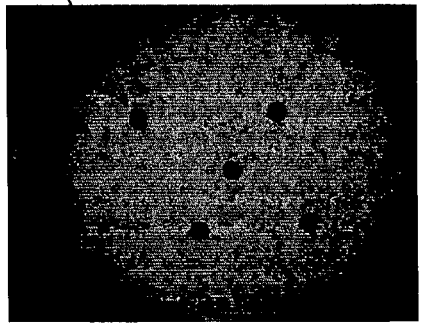
FIG. 1E is a micrograph of a coral scaffold prepared, which has a structure similar to that depicted in FIGS. 1A-1D.
Figure 2A:
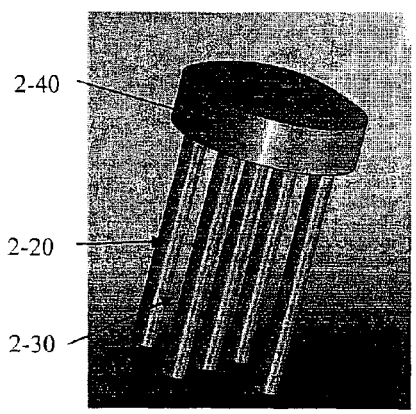
FIG. 2A shows a longitudinal filled in view of an embodiment of a scaffold of this invention. The scaffold comprises first regions 2-20 which are raised with respect to second regions 2-40, which first region in some embodiments is proximal to a void 2-30, which abuts the second region.
Figure 2B:
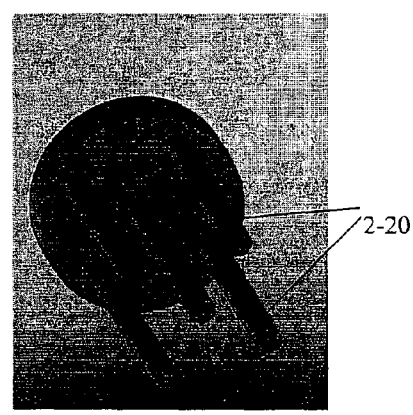
FIG. 2B shows an angled view of FIG. 2A.
Figure 2C:
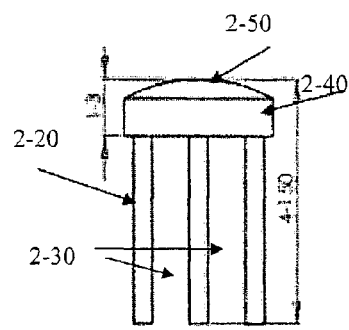
FIG. 2C shows a similar longitudinal cross-sectional view.
Figure 2D:
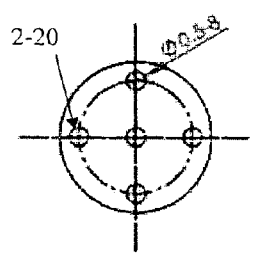
FIG. 2D shows a cross section of an edge of the scaffold in FIG. 2C.
Figure 4C:
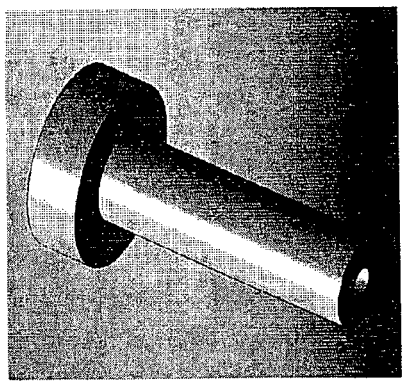
FIGS. 4A-F display three-dimensional images of scaffold geometries and longitudinal cross-sections of each.
Figure 4F:
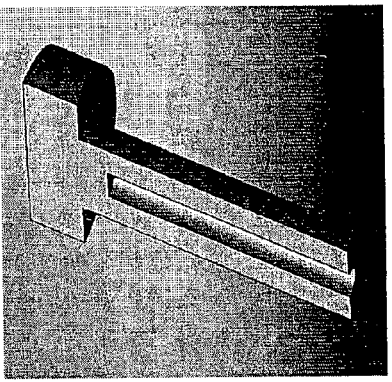
Figure 4B:
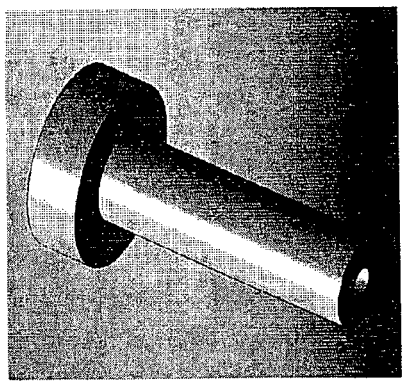
Figure 4E:
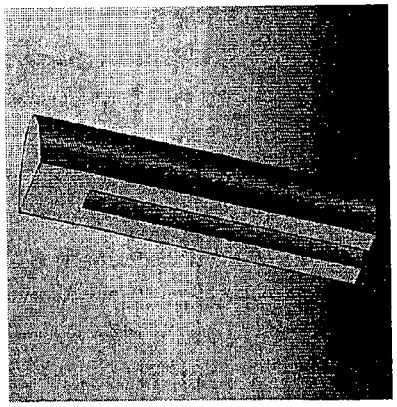
Figure 4A:
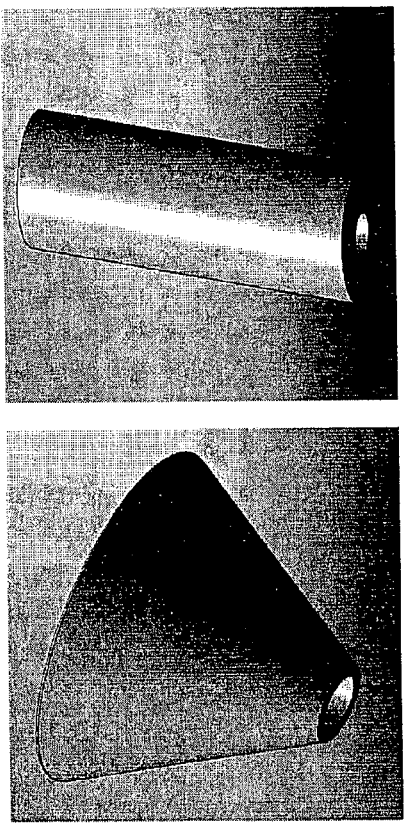
Figure 4D:
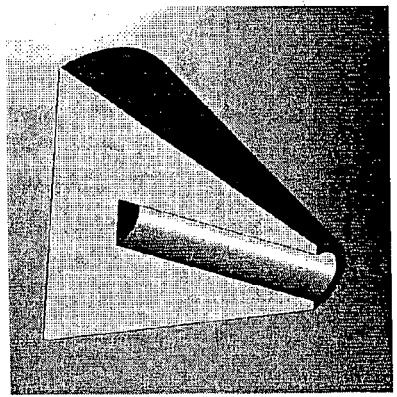

This invention provides, inter alia, scaffolds, tools and methods of use thereof for repair of cartilage tissue in a subject. This invention further provides kits for repair of cartilage tissue in a subject.

Coral, which is comprised of $CaCO_3$ in the crystalline form of calcite or aragonite, has the advantage of supporting fast cellular invasion, adherence, proliferation and differentiation of mesenchymal stem cells into cartilage tissue.

Three-dimensional (3-D) coral scaffolds attract mesenchymal stem cells from bone marrow and promote blood vessel formation to a site of cartilage repair. Such scaffolds can be used for regeneration of cartilage in a subject for repair of partial or full-thickness cartilage defects.

This invention provides the unexpected application of coral scaffolding alone being useful in cartilage repair and moreover, that coral scaffolding can be prepared and inserted specifically and optimally within a site of cartilage repair for methods of cartilage repair.

The terms "coral" and "aragonite" and "calcite" are used interchangeably herein.

In one embodiment, this invention provides a scaffold for repair of cartilage comprising coral having at least a first portion of an exposed surface raised with respect to at least a second portion of said exposed surface in the coral, wherein the first portion comprises at least a region, which specifically positions and confines the coral at an optimal depth and angle within a site of cartilage repair.

In one embodiment of this invention, the first portion comprises at least a region which specifically positions and confines the coral at an optimal depth and angle within a site of cartilage repair providing an arrangement between a scaffold of this invention and a site of cartilage repair which confers a benefit for cartilage repair.

In one embodiment, the term "specifically positions and confines the coral within a site of cartilage repair" refers to positioning at an optimal depth and angle by tight fitting, such that mechanical stress is sufficient to orient the implant optimally, or in some embodiments, the positioning is via a specific extension or protrusion of the scaffold, such that specific insertion into a region or wall of a tissue within a repair site, or within a site proximal to the repair site is accomplished. In some embodiments, multiple scaffolds are inserted therein, to optimally fill the defect site, or in some embodiments, to create a front or line along a defect site, leading from a region rich in repair cells and/or materials to a site most distal thereto, within a site for which cartilage repair is necessary.

It will be apparent to one skilled in the art that the physical and/or chemical properties of a scaffold of this invention and components thereof may influence methods of use of this invention and kits thereof, for inducing or enhancing cartilage repair.

In one embodiment, methods of this invention for inducing or enhancing cartilage repair utilize the 3-D geometry of a scaffold of this invention to provide for specifically positioning and confining the scaffold within a site of cartilage repair.

In one embodiment, the phrase "positions and confines" refers to the capacity of a region to secure a scaffold of this invention at a particular location within a site of cartilage repair.

In one embodiment, a region comprises a subdivision of an area into which the whole or one of its parts is divisible. In one embodiment, regions may share characteristics with each other.

In one embodiment, a site of cartilage repair may be considered to comprise a 3 dimensional (3-D) space at or proximal to a site of a cartilage defect or potential defect. In one embodiment, this 3-D space comprises at least a wall or a floor, or a combination thereof, and positioning within such a site may be described herein, relative to said wall or floor, or in some embodiments, positioning may be relative to insertion within a tissue site proximal to said wall or floor. In some embodiments, positioning include insertion of the scaffold or a region thereof, past the wall and/or floor of cartilage tissue or a site of defect or injury or potential defect or injury in the cartilage tissue, such that insertion into bone tissue occurs. In some embodiments, positioning optimizes access to blood vessels and a bone marrow, most proximal to the site of cartilage repair. In some embodiments, such positioning specifically inserts in a region within a bone marrow, which is not proximal to the site of repair, yet is a site which is enriched for mesenchymal stem cells, which participate in the repair.

In one embodiment, at least a region of the scaffold positions and confines the scaffold within a site of cartilage repair by forcefully contacting tissue at a site of or proximal to cartilage repair, wherein the scaffold is held in a specific position by the force of the region contacting the tissue. The force of contact between the scaffold and the tissue does not cause irreparable damage or unnecessary bleeding. For example if a site of cartilage repair is shaped like a cylindrical pit with a single continuous wall and a floor, regions of the representative scaffolds depicted in the figures may, in one embodiment, forcefully contact the tissue of the walls of the site to hold the 3-D scaffold in place. In one embodiment of this example, a bottom region of a scaffold, abuts a floor of a site of cartilage repair. In an alternative embodiment, forces exerted by regions of the scaffold contacting a wall of a site of cartilage repair hold and suspend the scaffold within the site such that it does not contact the floor. In such a case, a region of the scaffold may penetrate a wall of the site to reach a bone marrow void. In yet another embodiment, the forces exerted by the regions of the scaffold as described, position the scaffold such that if an additional raised region of the scaffold is present, this region now penetrates through bone and is stably inserted within a bone marrow void proximal to a site of cartilage repair.

In one embodiment, the term "proximal" refers to something being situated close to a particular locale. In one embodiment, a scaffold of this invention is forcibly held in position within a site of cartilage repair by a raised region of the scaffold contacting tissue situated at or proximal to a site of cartilage repair.

In some embodiments, the region of the scaffold which penetrates through bone and stably inserts within bone marrow is also the region of the scaffold which positions and confines the scaffold within a site of cartilage repair, or in some embodiments, the region of the scaffold which penetrates through bone and stably inserts within bone marrow is not the region which positions and confines the scaffold within a site of cartilage repair. FIGS. 1-3 show representative embodiments of a scaffold comprising a raised region of the exposed surface. If the site of cartilage repair is again shaped like a cylindrical pit with a single continuous wall and a floor, in one embodiment the second portion regions insert through the floor or wall of the site, and thereby penetrates through bone and is stably inserted within bone marrow proximal to a site of cartilage repair. In one embodiment, the region inserts through the floor or the wall so that the bottom of the main body of the scaffold makes contact with tissue at the site of cartilage repair. In one embodiment, the region inserts in such a way that no other portion of the scaffold is in contact with tissue at the site. In another embodiment, the region inserts in such a way that the side walls of the scaffold make contact with tissue at the site of cartilage repair.

One skilled in the art will recognize that the shape of a site of cartilage repair and the shape of a 3-D scaffold of this invention provide many different combinations for stably positioning a scaffold within a site of cartilage repair. In one embodiment, a scaffold of this invention is shaped prior to use in methods of this invention for cartilage repair. In one embodiment, a scaffold of this invention is shaped concurrent to use in methods of this invention for cartilage repair. By shaping a scaffold concurrent with use of the scaffold in methods of this invention, the dimensions of the scaffold may be precisely selected for specific positioning of the scaffold within a site of repair.

In one embodiment, a scaffold of this invention penetrates tissue situated close to or near a site of cartilage repair to reach a bone marrow proximal to the site of cartilage repair. In one embodiment, penetration of the bone marrow by a region of the scaffold positions and confines the scaffold independent of other regions of the scaffold. In one embodiment, penetration of the bone marrow by a region of the scaffold and forceful contact of at least an additional region of the scaffold with tissue at the site of repair together position and confine the scaffold. In one embodiment, penetration of the bone marrow by a region of the scaffold positions and confines the scaffold within a site of repair while at least an additional region of the scaffold passively contacts tissue at the site of repair.

As described above, a scaffold's region's ability to position and confine the scaffold of this invention is dependent on the region's geometry and the geometry at the site of cartilage repair where the scaffold will be implanted. In one embodiment, the region's geometry comprises a sharp edge. In one embodiment, the region's geometry comprises a rounded edge. In one embodiment, the region's geometry comprises a jagged edge.

In one embodiment, this invention comprises multiple raised portions with respect to other portions on the surface of a coral, and in some embodiments, at least a region of a multiple raised portion specifically positions and confines a coral at an optimal depth and angle within a site of cartilage repair. In some embodiments, the region of multiple raised portions is more suited for cartilage repair, and in some embodiments, the region which does not comprise raised portions is more suitable for bone repair, and the scaffolds of this invention are in some embodiments, particularly suited for the repair of osteochondral defects.

In one embodiment of this invention, an optimal depth and angle within a site of cartilage repair comprise the depth and angle most beneficial for cartilage repair. In one embodiment, the optimal depth and angle most beneficial comprise a position so that a scaffold of this invention is accessible to a pool of mesenchymal stem cells, a tissue milieu, blood vessels, nutrients, an effector compound, or a therapeutic compound, or a combination thereof.

In one embodiment of this invention, the term "depth" refers to a measurement of a scaffold of this invention extending from an imaginary line resting on the open surface of a repair site to a place beneath the tissue floor at a site of cartilage repair.

For example, based on a site of cartilage repair shaped like a cylindrical pit with a single continuous wall and a floor, in one embodiment a scaffold may be placed so that it extends through the floor, therefore, the depth of a region of the scaffold is below the floor, wherein the region penetrates into a bone marrow. This is beneficial for cartilage repair, since the bone marrow represents a source of mesenchymal stem cells. Moreover, other nutrients, effector compounds, or therapeutic compounds, or a combination thereof that may be found in the tissue milieu at or proximal to a site of repair, may now be in contact with the scaffold as it penetrates bone and other tissue to reach the bone marrow.

In one embodiment, the depth of a region of a scaffold may be below any tissue surface that lines a site of cartilage repair such that a region of the scaffold penetrates into a bone marrow.

It will be recognized by one skilled in the art that the depth of other regions of the scaffold may not be below any tissue surface. Based on a site of cartilage repair shaped like a cylindrical pit, an imaginary line drawn to rest across the opening of the pit represents the top of the pit. In one embodiment, positioning of the scaffold results in the entirety of the scaffold being below the top of the pit and therefore at a depth below the imaginary line across the opening. In one embodiment, positioning of the scaffold results in a portion of the scaffold being above the top of the pit and therefore not wholly within a site of cartilage repair. The benefit of placing a scaffold at a given depth may depend on the resulting contact the scaffold makes with surrounding tissue, either within the site of cartilage repair or proximal to the site of cartilage repair.

In one embodiment, the term "angle" refers to a measurement of the arc formed by an imaginary line along the long axis of the scaffold and an imaginary plumb line perpendicular to the line resting at the opening of a site of cartilage repair described above, with the arc progressing in a clockwise direction around this imaginary plumb line. Thus, in one embodiment a scaffold of this invention may be positioned and confined at an optimal depth and angle such that the scaffold is parallel to the perpendicular line, and therefore the angle would be 0 degrees. In one embodiment a scaffold of this invention may be positioned perpendicular to the imaginary plumb line, and therefore the angle would be 90 degrees. In one embodiment, the scaffold is positioned and confined at an angle equaling or less than 10 degrees. In one embodiment, the scaffold is positioned and confined at an angle equaling or less than 35 degrees. In one embodiment, the scaffold is positioned and confined at an angle equaling or less than 55 degrees. In one embodiment, the scaffold is positioned and confined at an angle equaling or less than 75 degrees. In one embodiment, the scaffold is positioned and confined at an angle equaling or less than 95 degrees. In one embodiment, the scaffold is positioned and confined at an angle equaling or less than 115 degrees. In one embodiment, the scaffold is positioned and confined at an angle equaling or less than 125 degrees. In one embodiment, the scaffold is positioned and confined at an angle of less than 145 degrees. In one embodiment, the scaffold is positioned and confined at an angle equaling or less than 165 degrees. In one embodiment, the scaffold is positioned and confined at an angle less than 180 degrees.

In some embodiments, multiple scaffolds are inserted to maximally occupy a defect site, such that each scaffold material may be inserted at a different angle, to accommodate proper insertion into the desired region within a site of cartilage repair. It is to be understood that the reference to angles of positioning above may be with regard to one or more scaffolds inserted in a particular cartilage defect site.

Contact between exposed surfaces of a scaffold and tissue at or proximal to a site of cartilage repair provides a bioactive surface which, in the methods of use of this invention may induce or enhance cartilage repair. For example, in one embodiment, the exposed surface of a scaffold provides a bioactive surface attracting mesenchymal stem cells. In another embodiment, the exposed surface provides a place for mesenchymal stem cell attachment, growth, proliferation, or differentiation, or a combination thereof, all processes which induce or enhance cartilage repair. In addition, the exposed surface of a scaffold may attract blood vessels. Moreover, tissue at or proximal to a site of cartilage repair may be a rich source of nutrients, effector compounds, therapeutic compounds, or a combination thereof, which may be beneficial in cartilage repair so that contact between an exposed surface of a scaffold and such tissue induces or enhances cartilage repair.

In one embodiment, the angle of placement of a scaffold is such that the scaffold is in contact with a region of a wall within a site of cartilage repair. In one embodiment, a scaffold of this invention may be positioned and confined such that there is maximal contact between the scaffold and tissues at or proximal to a site of cartilage repair. In one embodiment, a scaffold of this invention may be positioned and confined such that a region of the scaffold penetrates a bone marrow and there is maximal contact between the scaffold and tissues at or proximal to a site of cartilage repair. In one embodiment, contact between the exposed surface of the scaffold and the tissue at or proximal to a site of cartilage repair provides maximal surface area of the scaffold for interaction with a population of mesenchymal stem cells, blood vessels, effector compounds, or other components of a tissue milieu, or a combination thereof.

A scaffold of this invention may comprise multiple raised portions. It is possible for different portions of a scaffold to serve different functions. For example, in one embodiment a raised portion of a scaffold may penetrate a bone marrow, or a raised portion of a scaffold may hold the scaffold in place within a site of cartilage repair, or a raised portion of a scaffold may function as an exposed surface for attraction, growth, proliferation or differentiation of mesenchymal stem cells, or a raised portion of a scaffold may function to fit a tool of this invention, or any combination thereof.

In one embodiment, 100% of multiple raised portions specifically positions and confines a coral. In one embodiment, at least 80% of multiple raised portions specifically positions and confines a coral. In one embodiment, at least 60% of multiple raised portions specifically positions and confines a coral. In one embodiment, at least 40% of multiple raised portions specifically positions and confines a coral. In one embodiment, at least 20% of multiple raised portions specifically positions and confines a coral. In one embodiment, at least 10% of multiple raised portions specifically positions and confines a coral. In one embodiment, at least 1% of multiple raised portions specifically positions and confines a coral.

In one embodiment, placing and confining a scaffold of this invention at an optimal depth and angle within a site of cartilage repair provides for penetration of a portion of the exposed surface of the scaffold, through a bone tissue, resulting in the exposed surface inserting within a bone marrow proximal to a site of cartilage repair.

By optimizing the specific positioning of a scaffold the porous crystalline structure of a coral scaffolds of this invention, described below, is accessible to beneficial components located within a tissue milieu. For example, the porous crystalline structure of coral allows in-growth of blood vessels to create a blood supply for the cartilage that will infiltrate the scaffold during cartilage repair. By penetrating into a bone marrow, mesenchymal stem cells located within the bone marrow now have access to the exposed surface of the scaffold. In one embodiment, the region of the scaffold penetrating into a bone marrow attracts mesenchymal stem cells from the bone marrow and promotes blood vessel formation to the site of cartilage repair. In one embodiment, the region of the scaffold penetrating into a bone marrow promotes adhesion, proliferation, or differentiation or a combination thereof, of the mesenchymal stem cells attracted to the scaffold.

Thus, it will be apparent to one skilled in the art that the specific positioning of the scaffold within a site of cartilage repair arranges the scaffold of this invention such that the scaffold is most effective for cartilage repair.

In one embodiment, "scaffold" refers to a shaped platform used for cartilage repair, wherein the shaped platform provides a site for cartilage regeneration. In one embodiment, the scaffold is a temporary platform. In one embodiment, "temporary platform" refers to a natural degradation of a coral of this invention that occurs over time during cartilage repair, wherein the natural degradation of the coral may results in a change of scaffold shape over time, a change in scaffold size over time.

In one embodiment, the coral is shaped in the form of the tissue to be grown. For example, the coral can be shaped as a piece of cartilaginous tissue, such as a meniscus for a knee or elbow; a joint; an articular surface of a bone, the rib cage, a hip, a pelvis, an ear, a nose, the bronchial tubes and the intervertebral discs.

This invention provides, in some embodiments, coral scaffolds for use in repairing cartilage tissue defects associated with physical trauma, or cartilage tissue defects associated with a disease or disorder in a subject.

In one embodiment of this invention, the term "coral" refers to coral which is cut from a single piece of coral. In one embodiment, the coral has pore-like cavities or interstices.

In one embodiment, the coral scaffold is shaped prior to use in a method of cartilage repair. In one embodiment, the coral scaffold is shaped concurrent with a method of cartilage repair, e.g., the coral scaffold may be shaped during surgery when the site of repair may be best observed, thus optimizing the shape of the scaffold used.

In one embodiment, the scaffolds, methods and/or kits of this invention employ use of a coral. In one embodiment, the coral comprise any species, including, inter alia, *Porites, Acropora, Millepora*, or a combination thereof.

In one embodiment, the coral is from the *Porites* species. In one embodiment, the coral is *Porites Lutea*. In most species, the void to solid ratios is generally in the range of 0.4 to 0.6, and the void phase completely interconnects, forming a highly regular network that interpenetrates the solid calcium carbonate phase. In one embodiment, this uniform and interconnecting architecture is particularly useful as a framework in the scaffolds, methods and/or kits of this invention.

In one embodiment, the coral is from the *Acropora* species. In one embodiment, the coral is *Acropora grandis*, which in one embodiment is very common, fast growing, and easy to grow in culture. Thus, in one embodiment *Acropora* samples can be easily collected in sheltered areas of the coral reefs and collection from the coral reefs can be avoided by use of cultured coral material.

The average skeletal density of *Acropora grandis* is 2.7 g/ml. Because the skeleton of this coral species is dense and strong, it can be easily machined to a variety of configurations of shaped products or structures of different sizes, for example by grinding. This material is particularly suited for use in an implant device, in particular for weight-bearing joints such as knee and hip joints, where strength is an essential property of the implant device. Thus, in one embodiment, *Acropora* coral is useful as a framework in the scaffolds, methods and/or kits of this invention.

In another embodiment, the coral is from the *Millepora* species. In one embodiment, the coral is *Millepora dichotoma*. In one embodiment, the coral has a pore size of 150 µm and can be cloned and cultured, making *Millerpora* useful as a framework in the scaffolds, methods and/or kits of this invention.

In another embodiment, the coral is from any one or more of the following species: *Favites halicora; Goniastrea retiformis; Acanthastrea echinata; Acanthastrea hemprichi; Acanthastrea ishigakiensis; Acropora aspera; Acropora austera; Acropora* sp. "brown digitate"; *Acropora carduus; Acropora cerealis; Acropora chesterfieldensis; Acropora clathrata; Acropora cophodactyla; Acropora* sp. "danai-like"; *Acropora divaricata; Acropora donei; Acropora echinata; Acropora efflorescens; Acropora gemmifera; Acropora globiceps; Acropora granulosa; Acropora cf hemprichi; Acropora kosurini; Acropora cf loisettae; Acropora longicyathus; Acropora loripes; Acropora cf lutkeni; Acropora paniculata; Acropora proximalis; Acropora rudis; Acropora selago; Acropora solitaryensis; Acropora cf spicifera* as per Veron; *Acropora cf spicifera* as per Wallace; *Acropora tenuis; Acropora valenciennesi; Acropora vaughani; Acropora vermiculata; Astreopora gracilis; Astreopora myriophthalma; Astreopora randalli ; Astreopora suggesta; Australomussa rowleyensis; Coscinaraea columna; Coscinaraea crassa; Cynarina lacrymalis; Distichopora violacea; Echinophyllia echinata; Echinophyllia cf echinoporoides; Echinopora gemmacea; Echinopora hirsutissima; Euphyllia ancora; Euphyllia divisa; Euphyllia yaeyamensis; Favia rotundata; Favia truncata; Favites acuticollis; Favities pentagona; Fungia granulosa; Fungia klunzingeri; Fungia mollucensis; Galaxea acrhelia; Goniastrea edwardsi; Goniastea minuta; Hydnophora pilosa; Leptoseris explanata; Leptoseris incrustans; Leptoseris mycetoseroides; Leptoseris scabra; Leptoseris yabei; Lithophyllon undulatum; Lobophyllia hemprichii; Merulina scabricula; Millepora dichotoma; Millepora exaesa; Millipora intricata; Millepora murrayensis; Millipore platyphylla; Monastrea curta; Monastrea colemani; Montipora caliculata; Montipora capitata; Montipora foveolata; Montipora meandrina; Montipora tuberculosa; Montipora cf vietnamensis; Oulophyllia laevis; Oxypora crassispinosa; Oxypora lacera; Pavona bipartita; Pavona venosa; Pectinia alcicornis; Pectinia paeonea; Platygyra acuta; Platygyra pini; Platygyra* sp "green"; *Platygyra verweyi; Podabacia cf lanakensis; Porites annae; Porites cylindrica; Porites evermanni; Porites monticulosa; Psammocora digitata; Psammocora explanulata; Psammocora haimeana; Psammocora superficialis; Sandalolitha dentata; Seriatopora caliendrum; Stylocoeniella armata; Stylocoeniella guentheri; Stylaster* sp.; *Tubipora musica; Turbinaria stellulata*; or any coral known in the art, or a combination thereof.

In another embodiment, coral for use in the scaffolds, methods and/or kits of this invention may be *Madreporaria, Helioporida* of the order Coenothecalia, *Tubipora* of the order Stolonifera, *Millepora* of the order Milleporina, or others known in the art. In some embodiments, coral for use in the scaffolds, methods and/or kits of this invention may comprise scleractinian coral, including in some embodiments, *Goniopora* and others. In some embodiments, coral for use in the scaffolds, methods and/or kits of this invention may comprise *Alveoppora*. In some embodiments, coral for use in the scaffolds, methods and/or kits of this invention may comprise bamboo corals, including in some embodiments, coral from the family Isididae, genera *Keratoisis, Isidella*, and others.

In one embodiment, the size of a scaffold may be any size that would be useful for the purposes of the present invention, as would be known to one skilled in the art. In one embodiment, the scaffold or a portion thereof may be about the size of a site of cartilage repair. In one embodiment, the scaffold or a portion thereof may be about the size of a cartilage defect so that the scaffold may be placed within a site of cartilage repair. In another embodiment, the scaffold may be larger than the size of a cartilage defect. For example, in one embodiment, the scaffold of this invention may be larger than the size of a cartilage defect, whereby the scaffold may extend to a site of mesenchymal cell availability. In one embodiment, the scaffold may be smaller than the size of a cartilage defect.

In some embodiments, the scaffold size will be on a millimeter scale, for example, having at least one long axis of about 2-200 mm, or in some embodiments, about 1-18 mm, or in some embodiments, about 0.5mm-3 mm, or in some embodiments, about 6-12 mm, or in some embodiments, about 10-15 mm, or in some embodiments, about 12-40 mm, or in some embodiments, about 30-100 mm, or in some embodiments, about 50-150 mm, or in some embodiments, about 100-200 mm In one embodiment, the scaffold may be about the same size as a tissue void at a site of tissue repair. This tissue void may be due to a cartilage defect, cartilage degeneration or may have been created artificially during methods of cartilage repair or any combination thereof. In one embodiment, the tissue void comprises an absence of cartilage tissue. In one embodiment of this invention, the tissue void comprises an absence of cartilage and bone tissue. In one embodiment, the scaffold or a portion thereof may be the size of a cartilage defect such that the scaffold may be placed within a site of cartilage repair to enhance cartilage formation at the site of cartilage repair. In another embodiment, the scaffold may be larger than the size of a cartilage defect so that the scaffold may reach to a site of mesenchymal stem cell availability.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2.

In one embodiment, the term "void" refers to a space not occupied. In the instant invention, for example, in one embodiment, a void may be a space in a coral naturally not occupied. In one embodiment, a void may be a space not occupied at a site of repair. In one embodiment, a void may be a space not occupied within a scaffold of the current invention.

In one embodiment, a coral for use in a scaffold of this invention comprises an average pore size appropriate for seeding with precursor cells. In one embodiment, the average pore size of a coral is 1 µm-1 mm. In one embodiment, the average pore size of a coral is 30-180 µm In one embodiment, the average pore size of a coral is 50-500 µm. In one embodiment, the average pore size of a coral is 150-220 µm. In one embodiment, the average pore size of a coral is 250-1000 µm Processing of coral for use in scaffolds, methods of use, and kits thereof, may be as described in PCT International Application No. PCT/IL08/001511, which is incorporated by reference as if fully set forth herein. Further details in this respect are provided hereinunder.

In one embodiment, coral is purified from organic residues, washed, bleached, frozen, dried, sterilized or a combination thereof prior to seeding with precursor cells.

In one embodiment, scaffolds and scaffolds for use in the methods and kits of this invention are produced according to a process comprising washing naturally occurring coral sand with water to desalinate it, then disinfecting and drying the desalinated coral sand at temperatures of about 80° to about 150° C., preferably 90° to 120° C., and grinding the disinfected and dried coral into small particles, which in one embodiment comprise particles of 1-10 µm. In another embodiment, coral is ground into particles of 1-5, 1-20, 1-50, 1-100, 5-10, 10-15, 15-20, 10-50, 10-100, 20-100, 50-100, 80-150, 100-200, 100-350 or 150-500 µm.

Coral scaffolds of this invention comprise at least a first portion of an exposed surface raised with respect to at least a second portion of the exposed surface in the coral (FIGS. 1-3). The exposed raised surface may serve multiple functions with respect to methods of use of this invention and kits thereof. In one embodiment, a raised portion positions and confines a scaffold of this invention. In one embodiment, a raised portion penetrates through bone to insert within a bone marrow, thereby reaching a source of mesenchymal stem cells. In one embodiment, the exposed surfaces of raised and non-raised portions of the scaffold provide a site for the attraction, growth, proliferation or differentiation, or a combination thereof for mesenchymal stem cells In one embodiment of this invention, the term "portion" refers to a limited part of a whole.

In one embodiment, the term "portion of an exposed surface" refers to a limited part of a whole exposed surface. For example, in one embodiment a portion of an exposed surface comprises less than 100% of the exposed surface. In one embodiment a portion of an exposed surface comprises less than 90% of the exposed surface. In one embodiment a portion of an exposed surface comprises less than 80% of the exposed surface. In one embodiment a portion of an exposed surface comprises less than 70% of the exposed surface. In one embodiment a portion of an exposed surface comprises less than 60% of the exposed surface. In one embodiment a portion of an exposed surface comprises less than 50% of the exposed surface. In one embodiment a portion of an exposed surface comprises less than 40% of the exposed surface. In one embodiment a portion of an exposed surface comprises less than 30% of the exposed surface. In one embodiment a portion of an exposed surface comprises less than 20% of the exposed surface. In one embodiment a portion of an exposed surface comprises less than 10% of the exposed surface. In one embodiment a portion of an exposed surface comprises less than 1% of the exposed surface.

In one embodiment of this invention, the term "surface" refers to an exterior or upper boundary of an object.

In one embodiment of this invention, the term "exposed" refers to being open to the surrounding environment such that contact may occur between a coral scaffold of this invention and the surrounding environment. For example, in one embodiment the coral of this invention may be in contact with a surrounding environment comprising a site of cartilage repair, a tissue milieu, or a cell culture milieu.

In one embodiment, the term "exposed surface" refers to a surface of a coral being accessible/open/available, for instance to a site of cartilage repair. In one embodiment, the exposed surface may comprise a polymer coating, wherein the coating is accessible/open/available to a site of tissue repair. In one embodiment, an exposed surface of this invention is accessible to mesenchymal stem cells or to adjacent tissues that participate in the cartilage repair process, such as native cartilage and bone cells, such as chondrocytes, osteoblasts, osteoclasts, etc. In one embodiment, an exposed surface of this invention has access to effector compounds beneficial for cartilage repair. In one embodiment, an exposed surface of this invention may appear to be internal to the scaffold. In one embodiment, the term "internal" refers to those surfaces not easily seen from a particular external perspective; such surfaces comprise exposed surfaces within pore-like cavities or interstices of a coral and exposed surfaces of hollow spaces created within a coral, e.g., the internal exposed sections shown in the longitudinal cross-sections in FIG. 4, or the voids in FIGS. 1-3 comprise an exposed surface.

In one embodiment, the contact between the coral of this invention and the environment comprises the coral touching the environment. For example, in one embodiment the coral of this invention may touch the surface of a site of cartilage repair.

In one embodiment, methods of this invention may involve placement of a coral on a surface at site of cartilage repair. In one embodiment, methods of this invention may involve components of a tissue milieu at a site of coral repair migrating to an exposed surface of a coral and contact between the coral of this invention would be made thus with the environment.

In one embodiment, methods of this invention may involve implanting a scaffold so that raised exposed surfaces of the scaffold forcefully contact the tissue at or adjacent to a site of cartilage repair. In this way, the exposed surface of coral now proximal to a site of cartilage repair is proximal to an environment comprising cartilage tissue, bone tissue, bone marrow tissue, mesenchymal stem cells, nutrients, blood vessels or other effector compounds, or a combination thereof, which may be beneficial to cartilage repair.

In one embodiment, methods of this invention which provide for the contact of coral with the surrounding environment results in migration of mesenchymal cells, blood vessels, nutrients, therapeutic compounds or effector compounds, or a combination thereof beneficial to cartilage repair. In one embodiment, the contact of coral with mesenchymal stem cells occurs in an in vitro culture.

In one embodiment of this invention, the phrase "at least a first portion of an exposed surface raised with respect to at least a second portion of the exposed surface" refers to the first portion of an exposed surface projecting from a coral of this invention such that the first portion of the exposed surface comprises an elevation above at least a second portion of the exposed surface in the coral. It will be apparent to one skilled in the art that the first portion of an exposed surface raised with respect to at least a second portion of the exposed surface provides for increased overall surface area of a coral scaffold of this invention and provides for at least a region which specifically positions and confines said coral at an optimal depth and angle within a site of cartilage repair. In one embodiment, scaffolds of this invention are shaped to maximize exposed surface area.

In one embodiment of this invention, the exposed surface comprises multiple raised portions, with respect to other portions on said surface, e.g., the multiple raised portions on the exposed surface shown in FIG. 1, region 1-20, or FIG. 2, region 2-20 or FIG. 3, region 3-20. In one embodiment, the multiple raised portions provide for increased exposed surface area of a coral scaffold. In one embodiment, the multiple raised portions may each provide at least a region which specifically positions and confines said coral at an optimal depth and angle within a site of cartilage repair. In one embodiment, a single multiple raised portion provides at least a region which specifically positions and confines said coral at an optimal depth and angle within a site of cartilage repair. In one embodiment, at least 10% of the multiple raised portions provide at least a region which specifically positions and confines said coral at an optimal depth and angle within a site of cartilage repair. In one embodiment, at least 20% of the multiple raised portions provide at least a region which specifically positions and confines said coral at an optimal depth and angle within a site of cartilage repair. In one embodiment, at least 30% of the multiple raised portions provide at least a region which specifically positions and confines said coral at an optimal depth and angle within a site of cartilage repair. In one embodiment, at least 50% of the multiple raised portions provide at least a region which specifically positions and confines said coral at an optimal depth and angle within a site of cartilage repair. In one embodiment, at least 70% of the multiple raised portions provide at least a region which specifically positions and confines said coral at an optimal depth and angle within a site of cartilage repair. In one embodiment, at least 90% of the multiple raised portions provide at least a region which specifically positions and confines said coral at an optimal depth and angle within a site of cartilage repair. In one embodiment, 100% of the multiple raised portions provide at least a region which specifically positions and confines said coral at an optimal depth and angle within a site of cartilage repair.

In some embodiments, by adapting the dimensions, numbers, or placement, or a combination thereof, of the raised portions of a scaffold, the scaffold can be designed for use in methods and/or kits of this invention to induce or enhance cartilage repair, at sites of cartilage repair which may be vastly different from each other based on size, location, type of repair needed, type of defect present, or distance from the site to a bone marrow, or a combination thereof.

In one embodiment of this invention, the phrases "long axis of the scaffold" and longitudinal axis of the scaffold" are used interchangeably and refer to a line extending parallel to the scaffold lengthwise. The term "lengthwise" refers the direction of the length of a scaffold. It may be that an original geometric shape has been cut to produce a horizontal section of the original scaffold. In such instances lengthwise should be viewed as being the original direction of length along a scaffold.

In one embodiment, first multiple raised portions are positioned at a periodic distance with respect to each other on the surface. In one embodiment of this invention, the phrase "periodic distance" refers to a distance between multiple raised portions which comprises occurring or recurring regular intervals. In one embodiment, the periodic distance is the distance between facing junctions of one multiple raised portion on the surface with a directly adjacent multiple raised portion. In one embodiment, the periodic distance is the distance between the central long axis of one multiple raised portion on the surface with the central long axis of a directly adjacent multiple raised portion.

In one embodiment, first multiple raised portions are positioned at an aperiodic distance with respect to each other on the surface. In one embodiment of this invention, the phrase "aperiodic distance" refers to a distance between multiple raised portions which comprises irregular occurrences. In one embodiment, the aperiodic distance is the distance between facing junctions of one multiple raised portion on the surface with a directly adjacent multiple raised portion. In one embodiment, the aperiodic distance is the distance between a central long axis of one multiple raised portion on the surface with the central long axis of a directly adjacent multiple raised portion.

In one embodiment of this invention, the first multiple raised portions are of about equal height with respect to each other on the surface. In one embodiment, height comprises the furthest distance from the surface of a scaffold to the upper limit of a raised portion on the surface of the scaffold.

In one embodiment of this invention, the first multiple raised portions are of about unequal height with respect to each other on the surface.

In one embodiment of this invention, the first multiple raised portions are of about equal width with respect to each other on the surface. In one embodiment, width comprises a measurement along a horizontal line of the raised portion positioned at right angle to the long axis of the raised portion. In one embodiment of this invention, the first multiple raised portions have about equal widths for all horizontal lines with respect to each other on the surface.

In one embodiment, a multiple raised portion may have equal widths along any horizontal line of the raised portion with itself. In one embodiment, a multiple raised portion may have unequal widths along any horizontal line of the raised portion with itself.

In one embodiment of this invention, the first multiple raised portions are of unequal width with respect to each other on the surface. In one embodiment of this invention, the first multiple raised portions have unequal widths for all horizontal lines with respect to each other on the surface.

In one embodiment of this invention, the first multiple raised portions are positioned within a discrete region of the surface, wherein the discrete region does not cover 100% of the surface. In one embodiment of this invention, the first multiple raised portions are positioned within a discrete region of the surface, wherein the discrete region covers 50-100% of the surface. In one embodiment of this invention, the first multiple raised portions are positioned within a discrete region of the surface, wherein the discrete region covers less than 50% of the surface.

In one embodiment, a coral of this invention comprises a solid throughout a scaffold. One skilled in the art will recognize that solid coral of this invention still comprises pore-like cavities and/or interstices.

In one embodiment, a coral of this invention comprises a hollow along a Cartesian coordinate axis of a scaffold. In one embodiment, the hollow is along a long axis of a scaffold of this invention. In one embodiment, the term "hollow" refers to a cavity within a coral that results in a cavity within a scaffold of this invention. In one embodiment, the hollow comprises at least a single opening in the coral such that the cavity is exposed to the external environment. For example, FIGS. 1 and 2 show embodiments of scaffolds used in methods of this invention, wherein a series of hollows are present along the long axis of the representative scaffolds. In one embodiment, the hollow provides additional exposed surface area for a scaffold of this invention.

In some embodiments, such hollow or hollows may be constructed by any mechanical means, whereby the hollow/hollows is introduced. In some embodiments, such hollow creation may be by means of controlled drilling inward from a scaffold surface to a desired depth. In some embodiments, the specific creation of such hollows allows for ingrowth into the scaffold of appropriate cells involved in cartilage and/or bone repair, growth of blood vessels and other elements necessary for repair. In some embodiments, the hollows are specifically constructed within the scaffolds of the invention to be of a depth sufficient to span the cartilage area in which the scaffold is inserted to stimulate/enhance repair, and in some embodiments, such depth will not be sufficient to reach the bone.

In some embodiments, the scaffolds of this invention will comprise multiple hollows, which may be in any orientation, or in some embodiments, the scaffolds of this invention will comprise a network of hollows within scaffolds, or in some embodiments, multiple scaffolds are implanted into a repair site, wherein hollows of the scaffolds are aligned to form a network of hollows throughout the implanted scaffolds.

The exposed surface area of a scaffold of this invention provides a location for mesenchymal stem cell attachment, growth, proliferation or differentiation, or a combination thereof and a location for blood vessels formation. Therefore, the surface area of a scaffold of this invention ultimately provides a beneficial location for regeneration of cartilage tissue. Thus, it is advantageous to increase the surface area of a scaffold of this invention, for use in methods and kits of this invention. In one embodiment of this invention, a scaffold comprises a hollow, wherein the presence of the hollow increases the exposed surface area of a scaffold compared to an analogous scaffold without a hollow. In one embodiment, a scaffold comprises a coral cut with a hollow space to maximize surface area of the coral.

In one embodiment of this invention, the coral comprises a polymer coating. In one embodiment, a polymer coating strengthens the scaffold and/or enhance cartilage repair.

In one embodiment of this invention, a polymer coating is permeable. In one embodiment, the permeable polymer coating comprises a special porous membrane. In one embodiment, the term "permeable" refers to having pores and openings. In one embodiment, the permeable polymer coating of this invention has pores and openings which allow entry of nutrients, a therapeutic compound, a cell population, a chelator, or a combination thereof. In one embodiment, the permeable polymer coating of this invention has pores and openings which allow exit/release of nutrients, a therapeutic compound, a cell population, a chelator, or a combination thereof and/or blood vessels formation.

In one embodiment, a polymer coating of this invention is discontinuous. In one embodiment, a region or a plurality of sub-regions of the coral of this invention comprise an absence of polymer coating, allowing direct contact between the coral and the environment.

Figure 8A:
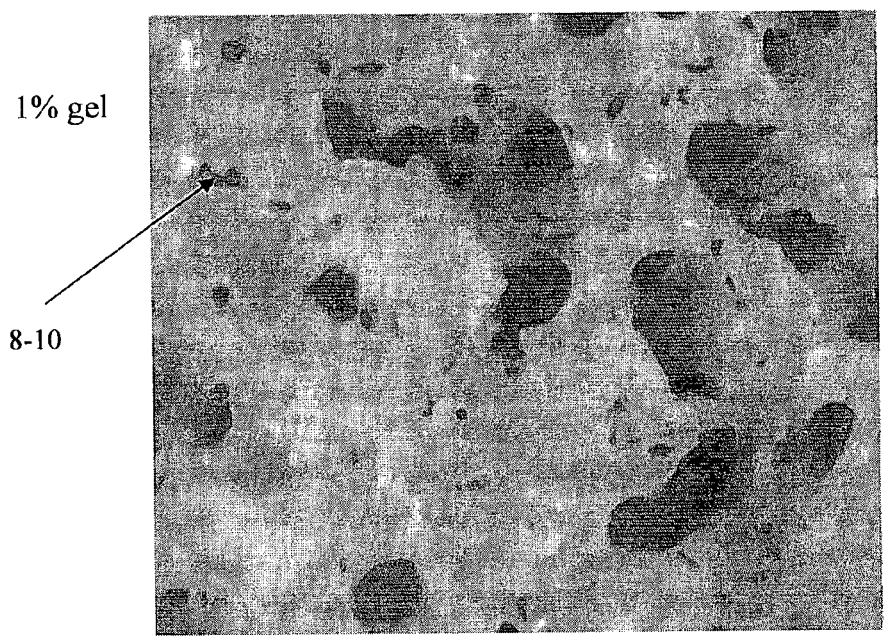
FIGS. 8A and 8B are photographs of scaffolds incorporating hyaluronic acid (HA) therewithin 8-10, following scaffold contact with solutions containing the HA at the indicated concentrations.
Figure 8B:
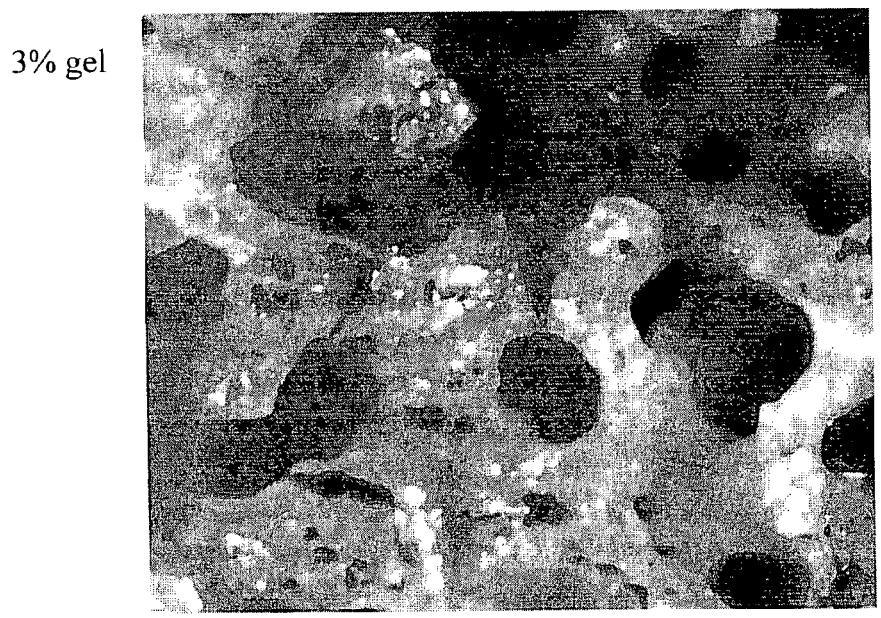

In one embodiment, a polymer coating of this invention may be a film, may take on the form of discontinuous particles and/or aggregates or a combination thereof. Example 2 and FIG. 8 herein describes the preparation of an embodiment of a scaffold of this invention incorporating hyaluronic acid particles, representing an embodiment of this invention In one embodiment, a polymer coating of this invention comprises a natural polymer comprising, collagen, elastin, silk, hyaluronic acid, chytosan, and any combinations thereof.

In one embodiment, the polymer comprises synthetically modified natural polymers, and may include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt.

In one embodiment, of this invention, a polymer comprises a synthetic biodegradable polymer. In one embodiment of this invention, a synthetic biodegradable polymer comprises alpha-hydroxy acids including poly-lactic acid, polyglycolic acid, enantioners thereof, co-polymers thereof, polyorthoesters, and combinations thereof.

In one embodiment, a polymer of this invention comprises a poly(cianoacrylate), poly(alkyl-cianoacrylate), poly(ketal), poly(caprolactone), poly(acetal), poly($\alpha$-hydroxy-ester), poly(a-hydroxy-ester), poly(hydroxyl-alkanoate), poly(propylene-fumarate), poly (imino-carbonate), poly(ester), poly (ethers), poly(carbonates), poly(amide), poly(siloxane), poly (silane), poly(sulfide), poly(imides), poly(urea), poly(amide-enamine), poly(organic acid), poly(electrolytes), poly(p-dioxanone), poly(olefin), poloxamer, inorganic or organomatallic polymers, elastomer, or any of their derivatives, or a copolymer obtained by a combination thereof.

In one embodiment, a polymer of this invention comprises poly(D,L-lactide-co-glycolide) (PLGA). In another embodiment, the polymer comprises poly(D,L-lactide) (PLA). In another embodiment, the polymer comprises poly(D,L-glycolide) (PGA). In one embodiment, the polymer comprises a glycosaminoglycan.

In one embodiment, the polymer comprises synthetic degradable polymers, which may include, but are not limited to polyhydroxy acids, such as poly(lactide)s, poly(glycolide)s and copolymers thereof; poly(ethylene terephthalate); poly(hydroxybutyric acid); poly(hydroxyvaleric acid); poly[lactide-co-($\epsilon$-caprolactone)]; poly[glycolide-co($\epsilon$-caprolactone)]; poly(carbonate)s, poly(pseudo amino acids); poly(amino acids); poly(hydroxyalkanoate)s; poly(anhydrides); poly(ortho ester)s; and blends and copolymers thereof.

In one embodiment of this invention, a polymer comprises proteins such as zein, modified zein, casein, gelatin, gluten, serum albumin, collagen, actin, $\alpha$-fetoprotein, globulin, macroglobulin, cohesin, laminin, fibronectin, fibrinogen, osteocalcin, osteopontin, osteoprotegerin, or others, as will be appreciated by one skilled in the art. In another embodiment, a polymer may comprise cyclic sugars, cyclodextrins, synthetic derivatives of cyclodextrins, glycolipids, glycosaminoglycans, oligosaccharide, polysaccharides such as alginate, carrageenan (χ, λ, μ, κ) chitosane, celluloses, condroitin sulfate, curdlan, dextrans, elsinan, furcellran, galactomannan, gellan, glycogen, arabic gum, hemicellulose, inulin, karaya gum, levan, pectin, pollulan, pullulane, prophyran, scleroglucan, starch, tragacanth gum, welan, xanthan, xylan, xyloglucan, hyaluronic acid, chitin, or a poly(3-hydroxyalkanoate)s, such as poly(β-hydroxybutyrate), poly(3-hydroxyoctanoate) or poly(3-hydroxyfatty acids), or any combination thereof.

In one embodiment, the polymer comprises a bioerodible polymer such as poly(lactide-co-glycolide)s, poly(anhydride)s, and poly(orthoester)s, which have carboxylic groups exposed on the external surface as the smooth surface of the polymer erodes, which may also be used. In one embodiment, the polymer contains labile bonds, such as polyanhydrides and polyesters.

In one embodiment, a polymer may comprise chemical derivatives thereof (substitutions, additions, and elimination of chemical groups, for example, alkyl, alkylene, hydroxylations, oxidations, and other modifications routinely made by those skilled in the art), blends of, e.g. proteins or carbohydrates alone or in combination with synthetic polymers.

In one embodiment of this invention, the polymer is biodegradable. In one embodiment, the term "biodegradable" or grammatical forms thereof, refers to a material of this invention, which is degraded in the biological environment of the subject in which it is found. In one embodiment, the biodegradable material undergoes degradation, during which, acidic products, or in another embodiment, basic products are released. In one embodiment, bio-degradation involves the degradation of a material into its component subunits, via, for example, digestion, by a biochemical process. In one embodiment, biodegradation may involve cleavage of bonds (whether covalent or otherwise), for example in a polymer backbone of this invention. In another embodiment, biodegradation may involve cleavage of a bond (whether covalent or otherwise) internal to a side-chain or one that connects a side chain to, for example a polymer backbone.

In one embodiment, a coral of this invention is covalently associated with the polymer coating via the use of a cross-linking agent. In one embodiment, the phrase "cross-linking agent" refers to an agent which facilitates the formation of a covalent bond between 2 atoms. In one embodiment, the cross-linking agent is a zero-length cross-linking agent.

In one embodiment, the cross-linking agent is (1 ethyl 3-(3dimethyl aminopropyl)carbodiimide (EDAC), N-Sulfohydroxy succinamide (Sulfo NHS), 5-iodopyrimidines, N-carbalkoxydihydroquinolines, pyrroloquinolinequinones, or a combination thereof.

In one embodiment, the cross-linking agent is a homobifunctional cross-linker, such as, for example, a N-hydroxysuccinimide ester (e.g. disuccinimidyl suberate or dithiobis (succinimidylpropionate), homobifunctional imidoester (e.g. dimethyladipimidate or dimethyl pimelimidate), sulfhydryl-reactive crosslinker (e.g. 1,4-di-[3'-(2'-pyridyldithio)propionamido]butane), difluorobenzene derivative (e.g. 1,5-difluoro-2,4-dinitrobenzene), aldehyde (e.g. formaldehyde, glutaraldehyde), bis-epoxide (e.g. 1,4-butanediol diglycidyl ether), hydrazide (e.g. adipic acid dihydrazide), bis-diazonium derivative (e.g. o-tolidine), bis-alkylhalide, or a combination thereof.

In one embodiment, the cross-linking agent is a heterobifunctional cross-linker, such as, for example, an amine-reactive and sulfhydryl-reactive crosslinker (e.g. N-succinimidyl 3-(2-pyridyldithio)propionate, a carbonyl-reactive and sulfhydryl-reactive crosslinker (e.g. 4-(4-N-maleimidophenyl) butyric acid hydrazide), or a combination thereof.

In some embodiments, the cross-linking agent is a trifunctional cross-linkers, such as, for example, 4-azido-2-nitrophenylbiocytin-4-nitrophenyl ester, sulfosuccinimidyl-2-[6-biotinamido]-2-(p-azidobenzamido)hexanoamido]ethyl-1, 3'-dithiopropionate (sulfo-SBED), or a combination thereof.

In another embodiment, the cross-linking agent is an enzyme. In one embodiment of this invention, the cross-linking agent comprises a transglutaminase, a peroxidase, a xanthine oxidase, a polymerase, or a ligase, or a combination thereof.

The choice of concentration of the cross-linking agent utilized for activity will vary, as a function of the volume, agent and polymer chosen, in a given application, as will be appreciated by one skilled in the art.

In one embodiment, the association of a coral of this invention with a polymer coating of this invention comprises a physical and/or mechanical association. For example, in one embodiment, a physical and/or mechanical association may comprise imbibing of any means, air drying, using a cross-linking agent, applying of heat, applying vacuum, applying lyophilizing methods, applying freezing, applying centrifuge, applying mechanical forces or any combination thereof, to promote the physical and/or mechanical association between a coral and a polymer coating as described herein.

It will be apparent to one skilled in the art that the physical and/or mechanical and/or chemical properties of a polymer coating and components thereof may influence methods of use of this invention and kits thereof, for inducing or enhancing cartilage repair.

In one embodiment, the polymer coating of this invention has a thickness of between 0.01 μm and 2.0 μm. In one embodiment, the polymer coating has a thickness of about 1.0 μm. In one embodiment, the polymer coating of this invention has a thickness of between 10 μm and 50 μm. In one embodiment, the polymer coating has a thickness of about 10-25, or about 15-30, or about 25-50 μm. In one embodiment, the polymer coating has a thickness of about 50-80, or about 60-90, or about 80-120 μm. In one embodiment, the polymer coating has a thickness of about 100-150, or about 130-200, or about 150-250 μm. In one embodiment, the polymer coating has a thickness of about 200-350, or about 300-600, or about 450-1000 μm. In some embodiments, multiple scaffolds comprising polymer coatings are implated into a repair site, wherein the coating thickness of a first scaffold may vary as compared to a coating thickness of a second scaffold, implanted in the repair site. Variations in the coating thickness may reflect the range described herein.

In one embodiment, the thickness of the polymer coating influences physical characteristics of a scaffold of this invention. For example, the thickness of a polymer coating may influence elasticity, tensile strength, adhesiveness, or retentiveness, or any combination thereof of a scaffold of this invention. In one embodiment, a polymer coating increases the elasticity of a scaffold of this invention. In one embodiment, a polymer coating increases the tensile strength of a scaffold of this invention. In one embodiment, the adhesiveness of a polymer coating relates to adhesion of mesencymal stem cells, blood vessels, tissue at a site of cartilage repair, cartilage tissue, or bone tissue, or a combination thereof. In one embodiment, a polymer coating decreases the adhesiveness of a scaffold of this invention. In one embodiment, a polymer coating increases the adhesiveness of a scaffold of this invention. One skilled in the art will recognize that a polymer coating may increase adhesiveness for an item while decreasing adhesiveness for another item. For example, in one embodiment, the polymer coating increases adhesiveness for a mesenchymal stem cell and decreases adhesiveness of an infective agent. In one embodiment, the retentiveness of a polymer coating relates to retention of a cell population. In one embodiment, the cell population retained within a polymer coating is a mesenchymal stem cell population. In one embodiment, the cell population retained within a polymer coating is a chondrocytes population. In one embodiment, the cell population retained within a polymer coating is an osteoblasts population. In one embodiment, the retentiveness of a polymer coating relates to retention of effector compounds.

In one embodiment, the thickness of the polymer coating influences proliferation and/or differentiation of mesenchymal stem cells. In one embodiment, the thickness of a polymer coating is selected to increase adhesion, proliferation, or differentiation, or a combination thereof, of mesenchymal stem cells with a scaffold of this invention during methods of use of the instant invention.

In one embodiment of this invention, the mesenchymal stem cells used in a scaffold, methods of use or kits thereof, are transformed.

In one embodiment, a polymer coating of this invention comprises an effector compound. In one embodiment, the effector compound is applied directly to a polymer coating of the scaffold of this invention. In one embodiment, the effector compound comprises a component of a kit of this invention for use for incorporation into a scaffold of this invention as herein described. In one embodiment, the effector compound is applied directly to a polymer coating of this invention, without being dispersed in any solvent.

In one embodiment of this invention, the polymer coating comprises an effector compound comprising a cytokine, a bone morphogenetic protein (BMP), a chelator, a cell population, a therapeutic compound, or an antibiotic, or any combination thereof.

In one embodiment, effector compounds for use in a scaffold and/or a kit of this invention and/or a method of this invention may comprise, inter-alia, a cytokine, a bone morphogenetic protein (BMP), a chelator, a cell population, a therapeutic compound, or an antibiotic, or any combination thereof.

In one embodiment, the phrase "a cell population" refers to a transfected cell population, a transduced cell population, a transformed cell population, or a cell population isolated from a subject, or a combination thereof. In some embodiments, transfected, transduced or transformed cells, may be incorporated into a polymer coat, a coral, coral particles or a scaffold of this invention, or a combination thereof.

In one embodiment, transfected, transduced or transformed cells, may be incorporated into a polymer coating, a coral, coral particles, a scaffold, or materials of this invention, so that engineered cells may comprise the polymer coating, coral, coral particles, scaffold, or materials of this invention.

In one embodiment, a cell population of this invention comprises mesenchymal stem cells. In one embodiment, the mesenchymal stem cells are transformed. In one embodiment, a cell population comprises cells beneficial in cartilage repair.

In one embodiment, the coral is seeded with a precursor cell. In one embodiment, the precursor cell is a mesenchymal stem cell. In other embodiments, the cell may be a mesenchymal cell; chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. In one embodiment of the present invention, the precursor cells for use in the method of the present invention are prepared from an organ tissue of the recipient mammal (i.e. autologous), or a syngeneic mammal. In another embodiment, allogeneic and xenogeneic precursor cells may be utilized.

In one embodiment of this invention, the phrase "a therapeutic compound" refers to a peptide, a protein or a nucleic acid, or a combination thereof. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses. In one embodiment, the therapeutic compound comprises a pro-angiogenic factor.

In one embodiment, the phrase "a therapeutic compound", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signaling cascade that provides for expression, or secretion, or others of a critical element for cellular or host functioning.

In another embodiment, the therapeutic compound may be natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the $\alpha$ family, transforming growth factors of the $\beta$ family, gastrins, secretins, cholecystokinins, somatostatins, serotonins, substance P, transcription factors or combinations thereof.

In one embodiment, a chelator of this invention comprises a Ca2+ chelator. In one embodiment, the calcium chelator is EDTA. In one embodiment, the chelator may comprise: ethylenediamine-N,N,N',N'-tetraacetic acid (EDTA), O,O'-bis(2-aminophenylethyleneglycol)ethylenediamine-N,N,N',N'-tetraacetic acid (BAPTA), N,N-bis(2-hydroxyethyl) glycine (Bicine), trans-1,2-diaminocyclohexane-ethylenediamine-N,N,N',N'-tetraacetic acid (CyDTA), 1,3-diamino-2-hydroxypropane-ethylenediamine-N,N,N',N'-tetraacetic acid (DPTA-OH), diethylenetriamine-N,N,N',N'',N''-pentaacetic acid (DPTA), ethylenediamine-N,N'-dipropionic acid dihydrochloride (EDDP), ethylenediamine-N,N'-bis(methylenephosphonic acid) hemihydrate (EDDPO), N-(2-hydroxyethyl)ethylenediamine-N,N',N'-triacetic acid (EDTA-OH), ethylenediamine-N,N,N',N'-tetrakis (methylenephosphonic acid) (EDTPO), O,O'-bis(2-aminoethyl) ethyleneglycol tetraacetic acid (EGTA), N,N'-bis(2-hydroxybenzyl)ethylenediamine-N,N'-diacetic acid (HBED), 1,6-hexamethylenediamine-N,N,N',N'-tetraacetic acid (HDTA), N-(2-hydroxyethyl)iminodiacetic acid (HIDA), iminodiacetic acid (IDA), 1,2-diaminopropane-N,N,N',N'-tetraacetic acid (methyl-EDTA), nitrilotriacetic acid (NTA), nitrilotripropionic acid (NTP), nitrilotris(methylenephosphonic acid) trisodium salt (NTPO), N,N,N',N'-tetrakis(2-pyridylmethyl)ethylenediamine (TPEN), and triethylenetetramine-N,N,N',N'',N''-hexaacetic acid (TTNA), rhod-2, DMSA, FLUO 3, FURA 2, INDO 1, QUIN 2, or other chelators known in the art, or a combination thereof.

In one embodiment, the effector compound comprises, an anti-helminth, an antihistamine, an immunomodulatory, an anticoagulant, a surfactant, a bronchodilator, an antibody, a beta-adrenergic receptor inhibitor, a calcium channel blocker, an ace inhibitor, a growth factor, a hormone, a DNA, an siRNA, or a vector or any combination thereof.

In one embodiment, the phrase "effector compound" refers to any agent or compound, which has a specific purpose or application which is useful in the treatment, prevention, inhibition, suppression, delay or reduction of incidence of infection, a disease, a disorder, or a condition, when applied to the scaffolds, kits and/or methods of this invention. An effector compound of this invention, in one embodiment, will produce a desired effect which is exclusive to the ability to image the compound. In some embodiments, the effector compound may be useful in imaging a site at which the compound is present, however, such ability is secondary to the purpose or choice of use of the compound.

In one embodiment of this invention, term "effector compound" is to be understood to include the terms "drug" and "agent", as well, when referred to herein, and represents a molecule whose incorporation within the scaffold and/or kits of this invention, or whose use thereof, is desired. In one embodiment, the agent is incorporated directly within a scaffold, and/or kit of this invention. In another embodiment, the agent is incorporated within a scaffold and/or kit of this invention, either by physical interaction with a polymer coating, a coral, or coral particles of this invention, and/or a kit of this invention, or association thereto.

In one embodiment, compounds for use in a scaffold and/or a kit of this invention and/or a method of this invention may comprise, inter-alia, an antibody or antibody fragment, a peptide, an oligonucleotide, a ligand for a biological target, an immunoconjugate, a chemomimetic functional group, a glycolipid, a labelling agent, an enzyme, a metal ion chelate, an enzyme cofactor, a cytotoxic compound, a bactericidal compound, a bacteriostatic compound, a fungicidal compound, a fungistatic compound, a chemotherapeutic, a growth factor, a hormone, a cytokine, a toxin, a prodrug, an antimetabolite, a microtubule inhibitor, a radioactive material, or a targeting moiety, or any combination thereof.

In one embodiment, the scaffolds and/or kits of this invention and/or methods of this invention comprise or make use of an oligonucleotide, a nucleic acid, or a vector. In some embodiments, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The scaffolds and/or kits of this invention and/or methods of use of this invention may comprise nucleic acids, in one embodiment, or in another embodiment, the scaffolds and/or kits of this invention and/or methods of use of this invention may include delivery of the same, as a part of a particular vector. In one embodiment, polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

In one embodiment, the scaffolds and/or kits of this invention and/or methods of this invention comprise or make use of a cell population. In one embodiment, the cell population is a mesenchymal stem cell population. In one embodiment, the mesenchymal stem cell population comprises a transformed mesenchymal stem cell population. In one embodiment, the cell may be chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. In one embodiment of the present invention, the precursor cells for use in the method of the present invention are prepared from an organ tissue of the recipient mammal (i.e. autologous), or a syngeneic mammal. In another embodiment, allogeneic and xenogeneic precursor cells may be utilized.

In one embodiment, the scaffold of this invention incorporates stem or progenitor or precursor cells. Such cells can be obtained directly from a mammalian donor, e.g., a patient's own cells, from a culture of cells from a donor, or from established cell culture lines. In some embodiments, the mammal is a mouse, rat, rabbit, guinea pig, hamster, cow, pig, horse, goat, sheep, dog, cat, monkey, ape or a human. Cells of the same species and/or of the same immunological profile can be obtained by biopsy, either from the patient or a close relative. Using standard cell culture techniques and conditions, the cells are then grown in culture until confluent and used when needed. The cells may be cultured until a sufficient number of cells have been obtained for a particular application.

In one embodiment, the scaffold of this invention incorporates any cell which may participate in cartilage repair. In some embodiments, such cells represent autografts, in that cells are cultured ex-vivo to seed the cells on the scaffolds of the invention, and such seeded scaffolds are implanted into the subject.

In some embodiments, such cells may represent allografts or xenografts, which may be incorporated within the scaffolds of this invention and implanted within a site of repair.

In one embodiment, a coral of this invention comprises a cell population from in vitro culture of the coral for a time period sufficient to seed the cells in the coral. In one embodiment, the cell population is a mesenchymal stem cell population. In one embodiment, the cell may be chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. In one embodiment of the present invention, the precursor cells for use in the method of the present invention are prepared from an organ tissue of the recipient mammal (i.e. autologous), or a syngeneic mammal. In another embodiment, allogeneic and xenogeneic precursor cells may be utilized. In one embodiment, the mesenchymal stem cells seeded in vitro are transformed. In one embodiment, the cell population comprises a cell population beneficial for cartilage repair. In one embodiment, the culture comprises a chelator. In one embodiment of this invention, the chelator in a culture comprises a calcium chelator.

In one embodiment, a method of this invention induces or enhances cartilage repair, wherein the method comprises implanting in a subject, a scaffold of this invention within a site of cartilage repair, wherein a region of the scaffold penetrates through a bone, resulting in the region inserting within a bone marrow, proximal to the site of cartilage repair.

In one embodiment, the phrase "cartilage repair" refers to restoring a cartilage defect to a more healthful state. In one embodiment, restoring cartilage results in regeneration of cartilage tissue. In one embodiment, restoring cartilage results in regeneration of a partial or full thickness articular cartilage defect. In one embodiment, restoring cartilage results in partial or complete regeneration of cartilage tissue at a site of cartilage repair. In one embodiment, cartilage repair may result in restoration/repair of missing or defective bone tissue as well. In one embodiment, cartilage repair comprises restoring cartilage defects of joints (e.g. knee, elbow, hip joints, shoulder, ankle), of ears, of a nose, or of a wind pipe.

In one embodiment, a method of this invention comprises inducing and enhancing cartilage repair wherein implanting a scaffold of this invention within a site of cartilage repair influences and improves cartilage repair.

In one embodiment, a method of this invention induces or enhances cartilage repair, by stably implanting a region of a scaffold within a bone marrow so that the region of the scaffold is now proximal to a site of enrichment of mesenchymal stem cells.

One skilled in the art will recognize that as methods of this invention implant a scaffold of this invention within a site of cartilage repair and wherein a region of the scaffold is inserted within a bone marrow , the scaffold formally connects the bone marrow tissue milieu with the site of cartilage repair.

In one embodiment, a method of this invention induces or enhances cartilage repair, wherein the region inserting within a bone marrow attracts a population of cells from the bone marrow to the scaffold, thereby influencing or improving cartilage repair. In one embodiment, a method of this invention induces or enhances cartilage repair, wherein the region inserting within a bone marrow attracts mesenchymal stem cells from the bone marrow.

The 3-D architecture and chemical composition of a coral scaffold of this invention are of great importance for both specifically positioning and confining a scaffold within a site of cartilage repair and for cellular recognition, adhesion, proliferation and differentiation of cell populations which induce or enhance cartilage repair. Example 3, described below, demonstrates that implanting a scaffold within a site of cartilage repair so that it forcibly contacts tissue at the site and is stably implanted within a bone marrow proximal to the site of cartilage repair, attracts mesenchymal stem cells to the scaffold and supports adhesion, growth, proliferation and differentiation of these mesenchymal stem cells into cartilage tissue without any need for additional growth promoting factors or any other inducers.

Therefore, in one embodiment a method of this invention induces or enhances cartilage repair, wherein implanting in a subject a scaffold of this invention promotes adhesion, proliferation or differentiation, or a combination thereof, of a cell population onto the scaffold. In one embodiment, a method of this invention induces or enhances cartilage repair, wherein implanting in a subject a scaffold of this invention promotes adhesion, proliferation or differentiation, or a combination thereof of mesenchymal stem cells from a bone marrow . In one embodiment, a scaffold of this invention utilized in a method of this invention comprises a seeded cell population prior to being implanted in a subject. In one embodiment, a method of this invention induces or enhances cartilage repair, wherein implanting in a subject a scaffold of this invention promotes adhesion, proliferation or differentiation, or a combination thereof of transformed mesenchymal stem cells. In one embodiment, a method of this invention induces or enhances cartilage repair, wherein implanting in a subject a scaffold of this invention promotes blood vessel formation.

In one embodiment, a method of this invention induces or enhances cartilage repair, wherein an exposed surface of a scaffold of this invention is maximized such that a cell populations has a maximal surface area for adhesion, growth, proliferation or differentiation, or a combination thereof. In one embodiment, a method of this invention induces or enhances cartilage repair, wherein an exposed surface of a scaffold of this invention is maximized such that maximal contact is made between the scaffold of this invention and a site of cartilage repair.

In one embodiment, a scaffold utilized in methods of this invention comprises at least a region which specifically positions and confines the coral scaffold at an optimal depth and angle within a site of cartilage repair, such that implanting the scaffold in a subject induces or enhances cartilage repair. In one embodiment, methods of this invention position and confine a scaffold of this invention within a site of cartilage repair such that a region of the scaffold comprises a stable insertion within a bone marrow. In one embodiment, methods of this invention comprise positioning a coral of this invention at an optimal depth and angle within a site of cartilage repair such that the depth and angle of the coral result in a region of a scaffold comprising a stable insertion within a bone marrow . In one embodiment, a scaffold utilized in methods of this invention comprises at least a region which specifically positions and confines the coral at an optimal depth and angle within a site of cartilage repair, such that implanting the scaffold maximizes the contact area between a scaffold of this invention and a site of cartilage repair.

In one embodiment, a scaffold utilized in methods of this invention comprises a shape comprising cylinder, cone, rectangular bar, plate, disc, pyramid, granule, ball, cube, tack, or a screw presented in FIG. 4.

In one embodiment, a scaffold utilized in a method of the present invention may be used to adsorb or bind, and deliver, other therapeutically active substances which assist in the cartilage repair or regeneration process, or which have other desired therapeutic activity. Such substances include, by way of example, known synthetic or semisynthetic antibiotics which may be introduced into the pore cavities of the shaped product or structure, or a growth factor such as transforming growth factor or one of the bone morphogenic proteins which can be used to assist or promote bone growth.

In any of the embodiments herein, scaffolds for use in the methods of the present invention may further comprise, or be implanted with, other compounds such as, for example, antioxidants, growth factors, cytokines, antibiotics, anti-inflammatories, immunosuppressors, preservative, pain medication, other therapeutics, and excipient agents. In one embodiment, examples of growth factors that may be administered in addition to the HMG-CoA reductase inhibitor include, but are not limited to, epidermal growth factor (EGF), transforming growth factor-alpha (TGF-$\alpha$), transforming growth factor-beta (TGF-$\beta$), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet derived growth factor (PDGF), or any combinations thereof. Examples of antibiotics include antimicrobials and antibacterials.

In one embodiment, a method of this invention comprises implanting a scaffold of this invention in a subject afflicted with a cartilage defect or disorder. In some embodiments, the scaffolds are particularly suitable for implantation in cartilage/bone defect via minimally invasive procedure, for example, arthroscopy.

In one embodiment, the term "implanting" refers to inserting and fixing a scaffold of this invention with in a living site in a subject, the site comprising a site of cartilage repair. In one embodiment, a method of this invention optimally implants a scaffold of this invention such that a region of the scaffold comprises a stable insertion within a bone marrow . In one embodiment, a method of this invention implants a scaffold such a region of the scaffold now has access to mesenchymal stem cells, nutrients, blood vessels, or effector compounds, or any combination there of. In one embodiment, a method of this invention comprises implanting in a subject a scaffold of this invention, wherein the method results in removing a region of a bone and/or other tissue so that a region of the scaffold penetrates through the bone and/or other tissue to reach a bone marrow.

A clinician skilled in the art will recognize that methods of this invention, which entail implanting a scaffold within a site of cartilage repair, may require preparation of a site of cartilage repair. These preparations may occur prior to implantation of a scaffold or simultaneously with implantation. For example, bone tissue and/or other tissues proximal to a site of cartilage repair may initially be drilled through to reach a bone marrow, creating a channel of dimensions appropriate for a scaffold used in the methods of this invention. Then the scaffold is implanted within the site so that a region of the scaffold penetrates the drilled bone tissue and extends into the bone marrow. Alternatively, the scaffold may be attached to a tool of this invention capable of penetrating through bone or other tissues, or a combination thereof. In this case, as the tool penetrates through the bone tissue to reach the bone marrow, the attached scaffold is simultaneously implanted so that a region of the scaffold penetrates into the bone marrow.

In some embodiments, following implantation of the scaffold within a repair site, or several scaffolds within the repair site, the scaffold is processed to optimize incorporation and optimal cartilage repair. In some embodiments, such processing may comprise cutting, sanding or otherwise smoothing the surface of the scaffold or scaffolds, for optimal repair.

In one embodiment, methods of this invention comprise implanting a scaffold in a human subject.

In one embodiment, methods of this invention comprise implanting a scaffold in a non-human mammalian subject. In one embodiment, methods of this invention comprise implanting a scaffold in a horse, a race horse, a cow, a steer, a pig, a sheep, a farm animal, a rabbit, a pet, a dog, a monkey, an ape, a bird or a cat.

In one embodiment, methods of this invention are utilized for induced or enhanced repair of a cartilage defect or disorder. In one embodiment, the cartilage defect results from a trauma, a tear, a sports injury, a full or partial thickness articular cartilage defect, a joint defect, avascular necrosis, osteochondral defect, or a repetitive stresses injury (e.g., secondary damage due to cruciate ligament injury). In one embodiment, the cartilage disorder comprises a disease of the cartilage or the subchondral bone. In one embodiment, methods of this invention induce or enhance cartilage repair in osteoarthritis, rheumatoid arthritis, aseptic necrosis, avascular necrosis, osteochondral defects, osteochondritis dissecans, articular cartilage injuries, chondromalacia patella, chondrosarcoma, chondrosarcoma—head and neck, costochondritis, enchondroma, hallux rigidus, hip labral tear, osteochondritis dissecans, torn meniscus, relapsing polychondritis, canine arthritis, fourth branchial arch defect or cauliflower ear. In one embodiment, methods of this invention induce or enhance cartilage repair in degenerative cartilagenous disorders comprising disorders characterized, at least in part, by degeneration or metabolic derangement of connective tissues of the body, including not only the joints or related structures, including muscles, bursae (synovial membrane), tendons, and fibrous tissue, but also the growth plate, meniscal system, and intervertebral discs.

In one embodiment, a cartilage defect or disorder repaired by the methods of this invention utilizing a scaffold and/or at least a tool of this invention, comprises a joint of a subject (e.g. a knee, elbow, ankle, shoulder or hip joint), a rotator cup, an ear, a nose, a windpipe, a pelvis, or any other site of cartilage defect found within the subject.

In one embodiment, the 3-D shape and chemical composition of a scaffold of this invention, used in the methods and/or kits of this invention will be determined by skilled clinicians, based on factors such as exact nature of the condition being treated, the severity of the condition, the age and general physical condition of the subject, body weight, and response of the individual subject, etc.

In one embodiment, the specific positioning of a scaffold of this invention during methods of this invention will be determined by skilled clinicians, based on factors such as exact nature of the condition being treated, the severity of the condition, the age and general physical condition of the subject, body weight, and response of the individual subject, etc.

In one embodiment, methods of this invention are evaluated by examining the site of cartilage tissue repair, wherein assessment is by histology, palpation, endoscopy, arthroscopy, or imaging techniques comprising X-ray photographs, computerized X-ray densitometry, computerized fluorescence densitometry, magnetic resonance imaging, or another method known in the art, or any combination thereof.

In one embodiment, this invention provides an instrument to aid in cartilage repair comprising a tool to guide a scaffold of this invention to an optimal angle at a site of cartilage repair, a tool to guide a scaffold of this invention to an optimal angle at a site of cartilage repair, a tool to deliver a scaffold of this invention to a site of cartilage repair, a tool to insert a scaffold of this invention at a site of cartilage repair so that the scaffold penetrates through a bone, and inserts within a bone marrow, proximal to said site of cartilage repair, a tool to release a scaffold of this invention at a site of cartilage repair, or a tool able to provide a combination thereof, whereby the tool may be separated from the scaffold following placement of the scaffold within a site of cartilage repair.

In one embodiment, the instrument of this invention comprises at least a single tool. Example 4 provides some examples of envisioned tools of this invention. The tools are versatile, in that, in one embodiment, a single tool may comprise 2 elements, which are useful for creating access to the cartilage/bone defect and inserting the scaffold therein, or in some embodiments, the same tool comprises different adaptor tips to achieve the same.

In one embodiment, methods of this invention utilize a tool of this invention such that at a site of cartilage repair preparations for implanting a scaffold of this invention comprise drilling through tissue to reach a bone marrow. In one embodiment, the tissue to be drilled is cartilage tissue, bone tissue, connective tissue, muscle tissue or bone marrow tissue or any combination thereof. One skilled in the art will recognize that selection of a tool will depend upon the tissue being penetrated.

In one embodiment, methods of this invention utilize an instrument of this invention, wherein implanting a scaffold of this invention comprises specifically positioning and confining the coral at an optimal depth and angle within a site of cartilage repair. Uniquely and representing one embodiment of the invention, the tools of this invention allow for implantation of the scaffold at a desired angle, or under arthroscopic conditions, in order to minimize for example, the risk of infection.

In some embodiments, such tools may comprise a tool for insertion of a scaffold into a repair site, which tool is specifically constructed to hold the scaffold and optimally position it within the site. In some embodiments, multiple tools for different sized or shaped scaffolds may be incorporated within kits of the invention, to accommodate the implantation of varied scaffolds within a site or sites of cartilage repair. In some embodiments, the kits of this invention will comprise a tool to process the scaffold following insertion within the site of repair, to effect a smooth optimal surface for optimal cartilage repair. In some embodiments, the kits of this invention may further comprise a tool for creating a void between the repair site and a source of mesenchymal stem cells. In some embodiments, the kits may comprise a piece, which inserts within a common tool to effect such a void, for example, a drill bit is included in the kits of this invention of a size and depth to easily and appropriately drill through nearby bone in order that the scaffolding may be inserted in a site of cartilage repair, where at least a portion of the scaffold, or contiguous scaffolds insert within a site of cartilage repair and reach underlying bone marrow, to serve as a source for migrating mesenchymal stem cells to effect cartilage repair One skilled in the art will recognize that the path created by drilling through tissue to reach a bone marrow is such that it allows for a scaffold of this invention to reach the bone marrow and be stably implanted at this site. The scaffold must be sufficiently secured within a site of cartilage repair so that it does not get dislodged as a joint articulates. A clinician skilled in the art will also recognize that the extent of a drilled path is such that a scaffold is securely held but the path is not so extensive to incur increased damage to surrounding tissue.

Preparation of a site of cartilage repair may also involve removing damaged cartilage or bone tissue, or a combination thereof. Therefore, in one embodiment, a tool of this invention drills a path such that damaged tissue at the site of repair or proximal to a site of repair is removed.

In one embodiment, a scaffold of this invention comprises a region fitted to a tool provided by an instrument of this invention. In one embodiment, the region fitted to a tool comprises cutting a single piece of coral to comprise a fitted region. In one embodiment, the region fitted to a tool comprises a region formed in a polymer coating.

A tool of this invention may therefore prepare the pathway a scaffold will follow, guide the scaffold being implanted, and implant the scaffold concurrently. By concurrently preparing the site and implanting the scaffold, the time of invasive surgery a subject is subjected to may be shortened.

In one embodiment, a region of the scaffold separates from the tool following placement of the scaffold within the site of cartilage repair. In one embodiment, the region separates from the tool, wherein separation of the tool from the scaffold comprises UV light-activated separation, LASER-activated separation, torsion-dependent separation or chemically-activated separation or a combination thereof. In one embodiment, separation of the tool from the scaffold leaves behind the scaffold specifically positioned within a site of repair for induced or enhance cartilage repair. The mechanism for separation should also not cause additional trauma to a site of repair.

In one embodiment, separation of the tool from the scaffold results in the scaffold being specifically positioned and confined at an optimal depth and angle within a site of cartilage repair. In one embodiment, separation of the tool from the scaffold results in the scaffold being implanted in a subject within a site of cartilage repair, wherein a region of the scaffold penetrates through a bone, results in the region inserting within a bone marrow, proximal to the site of cartilage repair.

In one embodiment, this invention provides a kit for repair of tissue comprising the scaffold of this invention, at least a tool of this invention, and directions for utilizing the scaffold in tissue repair.

One skilled in the art will recognize that choice of a kit by a skilled clinician would be dependent upon factors such as exact nature of the condition being treated, the severity of the condition, the age and general physical condition of the subject, body weight, and response of the individual subject.

Thus, in one embodiment, the scaffold comprised in a kit of this invention comprises different sizes, shapes or chemical compositions, or a combination thereof. In one embodiment, this invention provides a kit for cartilage repair comprising a scaffold of this invention, at least a tool of this invention, and directions for utilizing the scaffold in cartilage repair.

In one embodiment, methods of this invention utilize a scaffold of this invention with at least a tool of this invention to repair a site of cartilage repair in a subject, wherein a tool is used to drill within or proximal to a site of cartilage repair to provide access to a bone marrow, followed by the tool specifically implanting a scaffold of this invention within the site of cartilage repair, wherein a region of the scaffold penetrates into the bone marrow, wherein regeneration of cartilage or bone tissue or a combination thereof occurs. In one embodiment, methods of this invention may utilize a scaffold of this invention shaped at the time of drilling. In one embodiment, methods of this invention may simultaneously drill and implant a scaffold of this invention within a site of cartilage repair.

The architectural and chemical attributes of a 3-D coral scaffold of this invention so far described, may also be found in a scaffold formed from a polymer form enveloping coral particles. Therefore, in one embodiment, a scaffold of this invention for tissue repair comprises a polymer form enveloping coral particles.

In one embodiment, the polymer form comprises a flexible polymer form. In one embodiment of this invention, the term "flexible" refers to the capability of a polymer form to adapt to the requirements at a site of tissue repair. In one embodiment, the polymer form comprises a flexible polymer form at the time of implanting within a site of tissue repair and hardens over time. In one embodiment, the polymer form remains flexible for the life-time of the scaffold.

In one embodiment, a flexible polymer form adapts to the requirements at a site of tissue repair such that contact between a scaffold and a site of tissue repair is maximized. In one embodiment, a flexible polymer form adapts to the requirements at a site of tissue repair such that a region of a scaffold positions and confines the polymer envelope at an optimal depth and angle within a site of tissue repair. In one embodiment, a flexible polymer form adapts to the requirements at a site of tissue repair such that a region of a scaffold penetrates through a bone, resulting in the region inserting within a bone marrow, proximal to the site of tissue repair.

In one embodiment, the polymer form comprises a rigid polymer form. In one embodiment of this invention, the term "rigid" refers to a polymer envelope having a fixed framework. In one embodiment of this invention, a rigid polymer envelope may comprise all of the shape characteristics of a single piece of coral listed above.

In one embodiment, the polymer form maximizes surface area of the scaffold in contact with a site of implantation. In skilled in the art will recognize that similar to a scaffold shaped from a single piece of coral, maximizing surface area of a polymer form enveloping coral particles maximizes the area available to a mesenchymal stem cell populations at a site of tissue repair. In one embodiment, the maximal surface area is available to a mesenchymal stem cell population and/or chondrocytes and/or osteoblasts.

In one embodiment, the coral particles enveloped in a polymer forms are micronized to 1-10 µm or 5-20 µm or 10-50 µm in size.

In one embodiment, the coral particles comprise a same sources of coral as used for a scaffold comprising a single piece of coral.

In one embodiment, the polymer form of this invention comprises a same sources of polymer as used for a polymer coating of a single piece of coral.

In some embodiments, the term "comprise" or grammatical forms thereof, refers to the inclusion of the indicated components of this invention, as well as inclusion of other active agents, and pharmaceutically acceptable carriers, excipients, emollients, stabilizers, etc., as are known in the pharmaceutical industry.

In one embodiment, the present invention provides combined preparations. In one embodiment, the term "a combined preparation" defines especially a "kit of parts" in the sense that the combination partners as defined above can be used independently or in different combinations i.e., simultaneously, concurrently, separately or sequentially.

EXAMPLES

Example 1

Preparation of Coral Scaffolding

Coral is collected from the hydrocoral *Millepora dichotoma*, which has an average pore size of 150 µm and density of 1.7 g/cm³. Three-dimensional (3-D) coral scaffold implants of the desired shape are prepared from this material by first cutting and polishing the coral. This provides a shaped coral form without unwanted sharp edges. Following this mechanical processing, the coral is soaked twice in 4% HCl for 15 min each time, and is then treated with 4 M NaOH to remove trapped particles, debris and organic remnants. The coral is then autoclaved and treated by gas sterilization prior the surgical procedure.

The coral scaffold implants are inserted into osteochondral defects produced by drilling in the weight-bearing area of the medial femoral condyle of mature goats, sheep, horses, dogs and monkeys. The implants are tightly fitted into the defect and the excess length cut away to the level of the articular cartilage. In this way, the coral scaffold is grafted through two types of tissue, cartilage and subchondral bone.

The animal subjects are examined and observed over an extended time period, post arthroscopic surgery. The untreated knee of each animal is used as a control for comparisons following these surgeries. At appropriate intervals animals are sacrificed and necroscopy performed. Appropriate time periods for examining the site of cartilage repair are 4, 8, and 16 weeks post surgery. At this time, the articular surfaces are photographed and tissue is removed from the site of repair and prepared for histological observations. Specifically, a block consisting of the grafted area and the surrounding tissue is removed using a fine saw. The material is further processed for routine histology, which includes slow decalcification in 22% sodium citrate-buffered formic acid and staining of 5 mm thick transverse sections using haematoxylin and eosin.

Example 2

Coral Scaffolding Containing a Partial or Discontinuous Polymer Coating

Materials and Methods

Coralline scaffolds further comprising a hydrogel containing 1%, 3%, 5% and 10% hyaluronic acid (HA) were prepared.

1%, 3%, 5% and 10% hyaluronic acid (HA) solutions were prepared and mixed overnight on a shaker at room temperature. The resulting gels were applied to funnels containing tight-fitted coralline scaffolds/plugs and the amount of scaffold in contact with the gel varied. The funnel system was then spun in a centrifuge for 10-20 minutes at 10000 RPM, and scaffolds were then heated at 50° C. for 30 minutes, frozen at −80 ° C. for two hours and lyophilized at 30-40 mtorr, −100 ° C. overnight.

Results

FIG. 5A is a photograph showing scaffold insertion and tight fitting within a funnel as described, which results in exposure of a portion of the scaffold to what is applied to the funnel, as shown in FIG. 5B, where an HA hydrogel is applied to the funnel. In FIG. 5B, spinning the funnel containing scaffold with the HA hydrogel results in good incorporation of the hydrogel within the scaffold.

Varying the time and speed at which the funnel is spun controlled the penetration depth of the HA in the gel. FIG. 5E shows less penetration within the scaffold when the apparatus described was spun for 7 minutes, and FIG. 5D shows the penetration obtained when the apparatus was spun for 10 minutes, in comparison to 20 minutes, as shown in FIG. 5C. The staining evident is Safranin O, which stains hyaluronic acid incorporated in the scaffolds.

Figure 6:
FIG. 6 is a photograph of another embodied scaffold of this invention prepared as described herein, showing incorporation of the polymer within a specific region of the scaffold.
Figure 7:
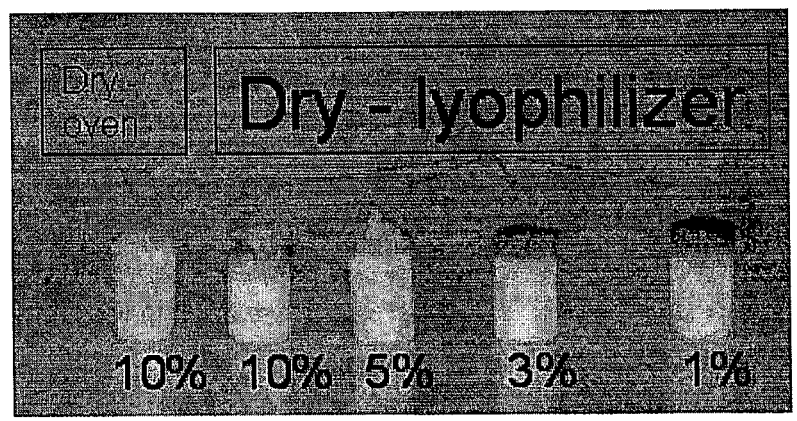
FIG. 7 is a photograph of various embodied scaffolds of the invention, which scaffolds have been dried by oven drying or lyophilization. The various percentages of hyaluronic acid solutions applied to the scaffolds prior to drying are shown.

Lyophilized scaffolds may be desired for use. FIGS. 6 and 7 depict lyophilized scaffolds, comprising an upper layer staining with Safranin O, and a lower layer without stain, indicating HA incorporation within the upper scaffold layer. In some embodiments of this invention, such scaffolds are desirable, whereby the HA-enriched layer is placed proximal to cartilage and the HA-deficient or poor layer is placed proximal to bone and/or in the bone marrow. FIG. 7 further depicts an oven-dried scaffold and the difference in HA distribution as a consequence of the drying method utilized.

Light microscopic evaluation of 1% (FIG. 8A) and 3% (FIG. 8B) HA scaffolds show HA particles 8-10 distributed in a dot pattern, coating the exposed surfaces of the scaffolds. For example: the average coated area of a 1% hydrogel scaffold preparation was about 2.3 square micro meter, while the average coated area in a 3% hydrogel scaffold was 3.4 square micro meter (about 50-70 spots evaluated).

Example 3

Restoration of an osteochondral defect

Figure 9A:
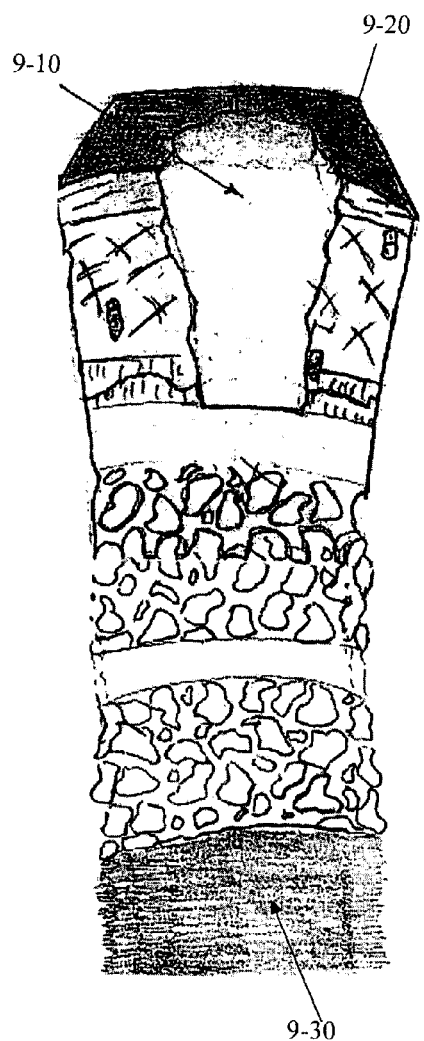
FIG. 9 shows implantation of a scaffold within a cartilage defect site.
Figure 9B:
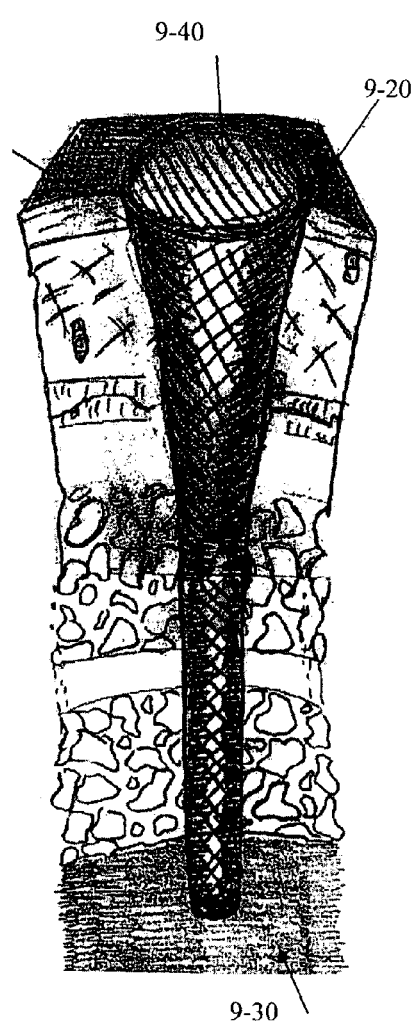

Restoration of an osteochondral defect is performed in mature dogs using rounded implants 3.5 mm in diameter and 6 mm in length A 3×7 mm core of cartilage and bone tissue is drilled out of the medial femoral condyle of each dog and the implant fitted into the site of cartilage repair (for example, as depicted in FIG. 9). Animals are harvested at variable time points post implantation; for example, 4, 8 and 16 weeks post surgery.

Analysis after one month shows that the implant is well incorporated into the articular cartilage creating a continuous smooth surface. The interface between the implant and the surrounding tissue is still visible, but the upper part of the implant has already been invaded and partial degradation of the implant material is observed. Histological sections reveal a void area in which the carbonated hydroskeletal material was decalcified.

Examination after two months shows some remnants of the biomaterial are still be detectable on the surface articular cartilage but well-defined organization of the chondral and subchondral tissue is also seen.

By 4 months, the implant material inserted in the chondral and subchondral area has been totally replaced by new cartilage and bone tissue. A well-defined tidemark is visible at the interface between the chondral and the subchondral tissue, and columnar chondrocytes and osteocytes are found in the subchondral area, similar to what is observed in a section taken from the untreated knee.

Example 4

Implantation Tools for Joint Repair

Figure 10A:
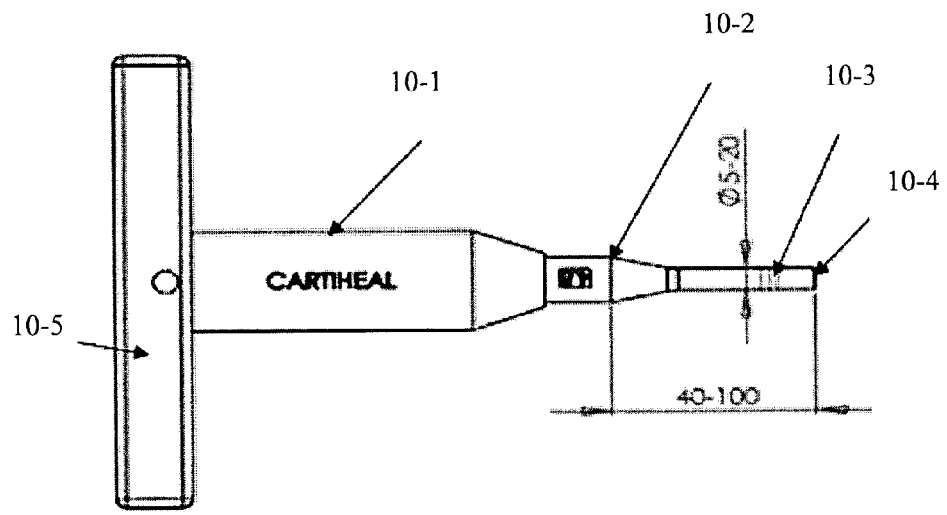
FIG. 10A shows a harvester 10-1 with a replaceable adaptor 10-4. The plunger or piston 10-5 is shown, as well. The tool may further comprise an indicator 10-3, which serves to delineate the depth at which the instrument is inserted.

Insertion of the scaffolds of this invention into a site of joint and/or bone repair may be via the use of specialized tools. A schematic example of one embodiment of a tool utilized in the insertion of a scaffold of this invention is depicted in FIG. 10. A harvester 10-1 has a replaceable adaptor which may contain a blade edge 10-4, which facilitates the penetration of cartilage and bone with the application of mechanical force. The tool may comprise a replaceable puncher head 10-5. The tool may further comprise an indicator 10-3, which serves to delineate the depth at which the instrument is inserted, and thereby avoid too deep insertion within the bone, or alternatively to indicate that the appropriate depth penetration has not been attained.

Figure 10B:
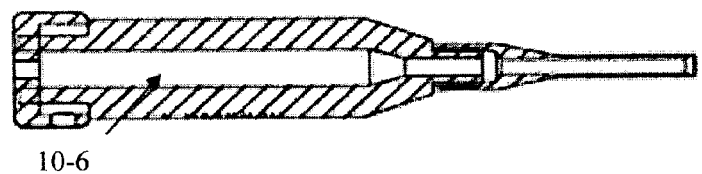
FIG. 10B shows a cross section along the long axis of the tool, which shows in this embodiment, the presence of a hollow extending along the length of the tool.
Figure 10C:
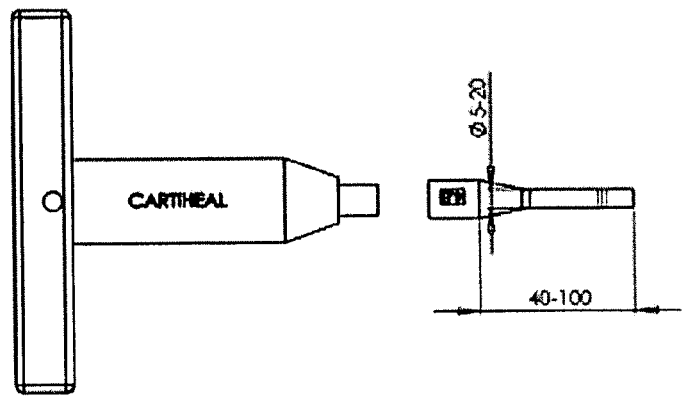
FIG. 10C shows a separated view of the tool in FIG. 10A.
Figure 12A:
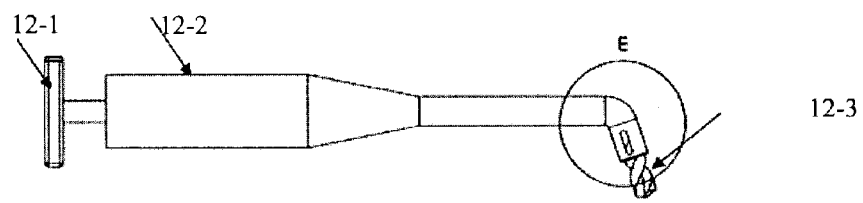
FIG. 12A depicts an angled tool comprising a plunger or piston 12-1 inserted in the body 12-2 of the tool, further comprising a joint 12-3, which can be either adjustable or replaceable with a different angle parts, for example, as depicted in FIGS. 12B and 12C, showing 12-4, which can be a replaceable locking head.
Figure 12B:
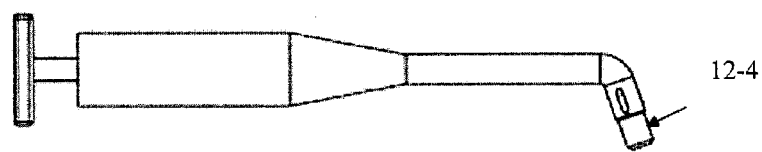
FIG. 12 schematically depicts an embodiment of an adjustable delivery system of this invention.
FIG. 12D provides an enlarged detailed view, where an adjustable or replaceable joint 12-5 is proximal to a groove, which may facilitate identification of positioning of the implant during implantation, which joint 12-6 may comprise a rounded edge 12-7 to minimize the trauma to tissue during implantation
Figure 12C:
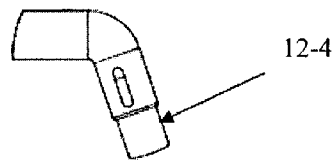
Figure 12D:
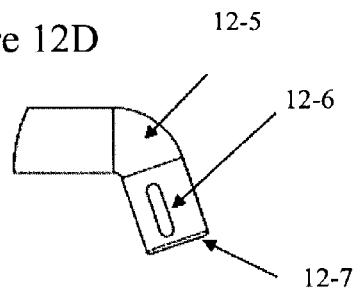

FIG. 10B demonstrates another embodiment of the tool, which shows a cross section along the long axis of the tool, which shows in this embodiment, the presence of a hollow extending along the length of the tool. Through this hollow, it is possible to insert a leading wire, such as a K-wire, or other leading device, which helps stabilize the tool during insertion of the scaffold, for example.

FIG. 11 schematically depicts another embodiment of a tool of this invention, in this case a tool insert, which may be inserted in the Harvester shown in FIG. 10A. The insertion body 11-2 depicted in FIG. 11A will further comprise a grooved hollow 11-3, which accommodates insertion of a scaffold within the hollow. The insertion body edge 11-4 may be modified to be smooth to avoid piercing any tissue during implantation of the scaffold contained therewithin. When the implant is loaded within the insert, the plunger or piston 11-1 pushes the implant out of the tool insert and into the site of repair, in for example, a hole made by the harvester of FIG. 10.

Figure 13A:
FIG. 13A shows a cross section along axis 13-1 -13-2 of the tool, which tool is semi-elastic. The elastic spring, or other strong and elastic material 13-3, transfers the force from the piston to the bit drill or to the inserted implant 13-4, as shown in FIG. 13B.
Figure 13B:
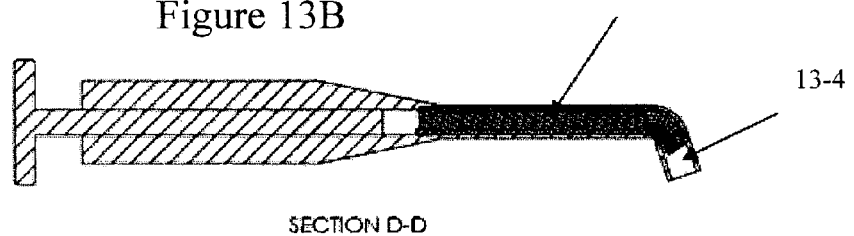
FIG. 13 depicts another embodied tool of the invention.

FIG. 12 schematically depicts an embodiment of an adjustable delivery system of this invention. FIG. 12A depicts the plunger or piston 12-1 placement within the body of the tool 12-2 which angles via attachment of a joint 12-3 about 50-2 mm from the edge providing easy access to a hard to reach areas, for example, inside the knee, when performing the arthroscopy or other procedures meant to be minimally invasive. This joint can be either adjustable or replaceable with a different angle parts, for example, as depicted in FIGS. 12B and 12C, showing 12-4, which can be a replaceable locking head. FIG. 12D provides an enlarged detailed view, where an adjustable or replaceable joint 12-5 is proximal to a groove, 12-6, which houses the implant during the implantation and which may facilitate identification of positioning of the implant during implantation, which joint may comprise a rounded edge 12-7 to minimize the trauma to tissue during implantation Another embodiment is shown in FIG. 13A, a cross section along axis 13-1 -13-2, which tool is semi-elastic. The elastic spring, or other strong and elastic material 13-3, transfers the force from the piston to the bit drill or to the inserted implant 13-4.

The insertion system is a syringe like system. The implant is loaded at the tip and the piston pushes the implant out and into the pre-created hole (defect) made by the harvester.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A scaffold for repair of cartilage or an osteochondral defect, said scaffold comprising coral having at least a first portion of an exposed surface, which first portion is raised with respect to at least a second portion of said exposed surface in said coral, wherein said at least a first portion of said coral is proximal to a hollow or hollows along a longitudinal axis of said first portion and wherein said at least a second portion abuts said hollow or hollows and wherein said first portion comprises at least a region, which specifically positions and confines said coral within a site of cartilage repair.

2. The scaffold of claim 1, wherein said coral comprises a polymer coating.

3. The scaffold of claim 2, wherein said polymer coating is permeable.

4. The scaffold of claim 2, wherein said polymer coating is discontinuous and optionally in the form of aggregates or particles.

5. The scaffold of claim 2, wherein said polymer comprises a natural polymer comprising collagen, elastin, silk, hyaluronic acid, chitosan, and any combinations thereof.

6. The scaffold of claim 5, wherein said collagen or hyaluronic acid is cross-linked.

7. The scaffold of claim 1, wherein said scaffold comprises a cytokine, a bone morphogenetic protein (BMP), a chelator, a cell population, a therapeutic compound, or an antibiotic, or any combination thereof.

8. The scaffold of claim 7, wherein said coral is seeded with a cell population and wherein said cell population comprises mesenchymal stem cells or osteoblasts or chondrocytes or other cells involved in cartilage repair or a combination thereof.

9. The scaffold of claim 7, wherein said therapeutic compound comprises an anti-inflammatory compound, an anti-infective compound, a growth factor, a pro-angiogenic factors or a combination thereof.

10. The scaffold of claim 1, wherein the scaffold comprises a shape comprising a cone, a tack, a screw, a cylinder, a rectangular bar, a plate, a disc, a pyramid, a granule, a ball or a cube.

11. The scaffold of claim 1, wherein at least a portion of said scaffold penetrates through a bone, resulting in said portion inserting within a bone marrow proximal to a site of cartilage or osteochondral repair.

12. A method of inducing or enhancing cartilage repair, said method comprising implanting in a subject, a scaffold of claim 1 within a site of cartilage repair in said subject, wherein a region of said scaffold penetrates through a bone, resulting in said region inserting within a bone marrow, proximal to said site of cartilage repair in said subject.

13. The method of claim 12, wherein said subject is afflicted with a cartilage defect or disorder wherein said cartilage defect or disorder comprises a full or partial thickness articular cartilage defect, osteoarthritis, osteochondritis, avascular necrosis, a joint defect or a defect resulting from trauma, sports, diseases or repetitive stress.

14. A method of treating an osteochondral defect in a subject, said method comprising implanting in a subject, a scaffold of claim 1 within a site of osteochondral defect in said subject, wherein a region of said scaffold penetrates through a bone, resulting in said region inserting within a bone marrow, proximal to said site of osteochondral defect in said subject.

15. A scaffold for tissue repair, said scaffold comprising a polymer form enveloping coral particles, wherein said scaffold is rigid and has at least a first portion of an exposed surface, which first portion is raised with respect to at least a second portion of said exposed surface in said coral, wherein said at least a first portion of said coral is proximal to a hollow or hollows along a longitudinal axis of said first portion and wherein said at least a second portion abuts said hollow or hollows and wherein said first portion comprises at least a region, which specifically positions and confines said coral within a site of cartilage repair.

16. The scaffold of claim 15, wherein said polymer comprises a natural polymer comprising collagen, elastin, silk, hyaluronic acid, chitosan, and any combinations thereof.

17. The scaffold of claim 15, wherein said polymer form is flexible.

18. The scaffold of claim 15, wherein said polymer enhances cartilage or bone formation or repair.

19. The scaffold of claim 15, wherein said coral particles are micronized to 1-10 μm or 5-20 μm or 10-50 μm in size.

20. The scaffold of claim 15, wherein said polymer is permeable.

21. The scaffold of claim 15, wherein said scaffold comprises an anti-inflammatory compound, an anti-infective compound, a growth factor, a pro-angiogenic factor or a combination thereof.

22. The scaffold of claim 15, comprising a pasting agent.

23. The scaffold of claim 22, wherein said pasting agent comprises a native or cross linked hyaluronan (HA), collagen or fibrinogen.

24. The scaffold of claim 15, wherein said scaffold comprises a cytokine, a bone morphogenetic protein (BMP), a chelator, a cell population, a therapeutic compound, or an antibiotic, or any combination thereof.

25. The scaffold of claim 1, wherein said scaffold lacks a polymer coating.

26. The scaffold of claim 1, wherein the hollow or hollows increase the exposed surface area of the scaffold.

* * * * *